US 6,337,305 B1

(12) United States Patent
Schäfer et al.

(10) Patent No.: US 6,337,305 B1
(45) Date of Patent: Jan. 8, 2002

(54) SUBSTITUTED 2-BENZ(O)YLPYRIDINES, THEIR PREPARATION AND THEIR USE AS HERBICIDES

(75) Inventors: Peter Schäfer, Ottersheim; Gerhard Hamprecht, Weimheim; Markus Menges, Bensheim; Olaf Menke, Altleiningen; Michael Rack, Heidelberg; Cyrill Zagar, Ludwigshafen; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/381,033

(22) PCT Filed: Mar. 9, 1998

(86) PCT No.: PCT/EP98/01354

§ 371 Date: Sep. 15, 1999

§ 102(e) Date: Sep. 15, 1999

(87) PCT Pub. No.: WO98/42671

PCT Pub. Date: Oct. 1, 1998

(30) Foreign Application Priority Data

Mar. 20, 1997 (DE) .......................... 197 11 569

(51) Int. Cl.$^7$ ................. C07D 213/30; C07D 213/55; C07D 213/61

(52) U.S. Cl. ................. 504/244; 546/342; 546/343; 546/344

(58) Field of Search ............... 546/341, 342, 546/343, 344; 504/244

(56) References Cited

U.S. PATENT DOCUMENTS

| 3,225,054 A | 12/1965 | Cusic | 546/333 |
|---|---|---|---|
| 4,564,381 A | 1/1986 | Bieringer et al. | 504/267 |

FOREIGN PATENT DOCUMENTS

| CA | 2190699 | 6/1997 |
|---|---|---|
| CH | 642 075 | 3/1984 |
| DE | 29 48 095 | 6/1981 |
| EP | 047 972 | 3/1982 |
| EP | 978 536 | 5/1983 |
| EP | 303 415 | 2/1989 |
| EP | 461 079 | 12/1991 |
| EP | 778 264 | 6/1997 |
| WO | 92/22203 | 12/1992 |
| WO | 97/17829 | 6/1996 |
| WO | 96/33168 | 10/1996 |

OTHER PUBLICATIONS

J. Med. Chem. 1991, 34, 1314–1328, Sleevi et al.
J. Chem. Soc., Perkin Trans 1, 1996, Kondo et al., 1781.
Antiviral Res., 7(1987) 87–97, Kenny et al.
Biosci. Biotech. Biochem., 57 (2), 350–351, 1993, Asami et al.

Primary Examiner—Alan L. Rotman
(74) Attorney, Agent, or Firm—Keil & Weinkauf

(57) ABSTRACT

Substituted 2-benz(o)ylpyridines I

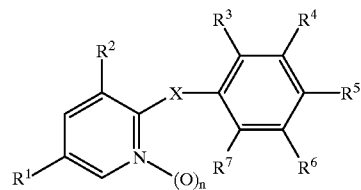

and salts thereof where n=0, 1;

X=CO, $CH_2$, CH($C_1$–$C_4$-alkyl), CH—OH, CH—CN, CH-halogen, C(halogen)$_2$, CH—$CONH_2$, CH—CO—O($C_1$–$C_4$-alkyl), CH—O($C_1$–$C_4$-alkyl), C(CN)($C_1$–$C_4$-alkyl);

$R^1$=halogen, $C_1$–$C_4$-haloalkyl, $C_1$–$C_4$-alkylthio, $C_1$–$C_4$-alkylsulfinyl, $C_1$–$C_4$-alkylsulfonyl;

$R^2$=H, halogen;

$R^3$=H, $NO_2$, OH, halogen, $C_1$–$C_4$-alkoxy;

$R^4$=H, $NO_2$, OH, halogen, $C_1$–$C_4$-alkyl, $C_1$–$C_4$-haloalkyl, $C_1$–$C_4$-alkoxy;

$R^5$=H, $NO_2$, CN, halogen, $C_1$–$C_8$-alkyl, $C_3$–$C_8$-alkenyl, $C_3$–$C_8$-alkynyl, $C_3$–$C_8$-cycloalkyl, $C_1$–$C_8$-haloalkyl, $C_2$–$C_8$-haloalkenyl, $C_2$–$C_8$-haloalkinyl, $C_1$–$C_4$-alkoxy-$C_1$–$C_4$-alkyl, $C_2$–$C_4$-alkenyloxy-$C_1$–$C_4$-alkyl, $C_2$–$C_4$-alkynyloxy-$C_1$–$C_4$-alkyl, $C_1$–$C_4$-alkylthio-$C_1$–$C_4$-alkyl, $C_1$–$C_4$-alkylsulfinyl-$C_1$–$C_4$-alkyl, $C_1$–$C_4$-alkylsulfonyl-$C_1$–$C_4$-alkyl, cyano-$C_1$–$C_8$-alkyl, cyano-$C_2$–$C_8$-alkenyl, cyano-$C_3$–$C_8$-alkynyl, unsubstituted or substituted OH, SH, SO—H, —$SO_2$—H, COOH or NH—COOH, —$SO_2$Cl, —N($R^9$,$R^{10}$), —NH—$SO_2$—($C_1$–$C_8$-alkyl), —N[—$SO_2$—($C_1$–$C_8$-alkyl)]$_2$, —N($C_1$–$C_8$-alkyl)[—$SO_2$—($C_1$–$C_8$-alkyl)], —$SO_2$—N($R^9$,$R^{10}$), —O—CO—NH—$R^9$, unsubstituted or substituted CHO, —O—CHO or —NH—CHO, —NH—CO—NH—$R^9$, —O—CS—$NH_2$, —O—CS—N($C_1$–$C_8$-alkyl)$_2$, —CO—N($R^9$,$R^{10}$), —CS—N($R^9$, $R^{10}$), —CO—NH—$SO_2$—($C_1$–$C_4$-alkyl).

7 Claims, No Drawings

SUBSTITUTED 2-BENZ(O)YLPYRIDINES, THEIR PREPARATION AND THEIR USE AS HERBICIDES

CROSS-REFERENCE

This application is a § 371 of PCT/EP98/01354 filed Mar. 09, 1998.

The present invention relates to novel substituted 2-benz(o)ylpyridines of the formula I

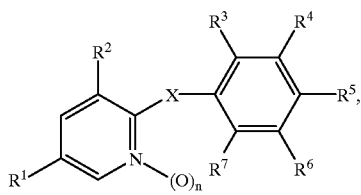

where
- n is 0 or 1;
- X is carbonyl, methylene, CH($C_1$–$C_4$-alkyl), CH—OH, CH—CN, CH-halogen, C(halogen)$_2$, CH—CONH$_2$, CH—CO—O($C_1$–$C_4$-alkyl), CH—O($C_1$–$C_4$-alkyl) or C(CN) ($C_1$–$C_4$-alkyl);
- $R^1$ is halogen, $C_1$–$C_4$-haloalkyl, $C_1$–$C_4$-alkylthio, $C_1$–$C_4$-alkylsulfinyl or $C_1$–$C_4$-alkylsulfonyl;
- $R^2$ is hydrogen or halogen;
- $R^3$ is hydrogen, nitro, hydroxyl, halogen, or $C_1$–$C_4$-alkoxy;
- $R^4$ is hydrogen, nitro, hydroxyl, halogen, $C_1$–$C_4$-alkyl, $C_1$–$C_4$-haloalkyl or $C_1$–$C_4$-alkoxy;
- $R^5$ is hydrogen, nitro, cyano, halogen, $C_1$–$C_8$-alkyl, $C_3$–$C_8$-alkynyl, $C_3$–$C_8$-alkynyl, $C_3$–$C_8$-cycloalkyl, $C_1$–$C_8$-haloalkyl, $C_2$–$C_8$-haloalkenyl, $C_2$–$C_8$-haloalkynyl, $C_1$–$C_4$-alkoxy-$C_1$–$C_4$-alkyl, $C_2$–$C_4$-alkenyloxy-$C_1$–$C_4$-alkyl, $C_2$–$C_4$-alkynyloxy-$C_1$–$C_4$-alkyl, $C_1$–$C_4$-alkylthio-$C_1$–$C_4$-alkyl, $C_1$–$C_4$-alkylsulfinyl-$C_1$–$C_4$-alkyl, $C_1$–$C_4$-alkylsulfonyl-$C_1$–$C_4$-alkyl, cyano-$C_1$–$C_8$-alkyl, cyano-$C_2$–$C_8$-alkenyl, cyano-$C_3$–$C_8$-alkynyl, —OR$^8$, —SR$^8$, —SO—R$^8$, —SO$_2$—R$^8$, —SO$_2$Cl, —N($R^9$,$R^{10}$), —NH—SO$_2$—($C_1$–$C_8$-alkyl), —N[—SO$_2$—($C_1$–$C_8$-alkyl)]$_2$, —N($C_1$–$C_8$-alkyl)[—SO$_2$—($C_1$–$C_8$-alkyl)], —SO$_2$—N($R^9$,$R^{10}$), —N($R^{11}$)—CO—$R^{12}$, —NH—CO—OR$^8$, —O—CO—NH—$R^9$, —O—CO—$R^{12}$, —NH—CO—NH—$R^9$, —O—CS—NH$_2$, —O—CS—N($C_1$–$C_8$-alkyl)$_2$, —CO—OR$^8$, —CO—N($R^9$,$R^{10}$), —CS—N($R^9$,$R^{10}$), —CO—NH—SO$_2$—($C_1$–$C_4$-alkyl), —CO—N($C_1$–$C_4$-alkyl)—SO$_2$—($C_3$–$C_4$-alkyl), —CO—$R^{12}$, hydroxycarbonyl-$C_1$–$C_8$-alkyl, ($C_1$–$C_8$-alkoxy)carbonyl-$C_1$–$C_6$-alkyl, —CH$_2$—CH(halogen)—CO—OR$^8$, —CH$_2$—CH(halogen)—CO—N($R^9$,$R^{10}$), —CH$_2$—CH(halogen)—CN, —CH$_2$—CH(halogen)—CO—($C_1$–$C_4$-alkyl), —CH═C(halogen)—CO—OR$^8$, —CH═C($C_1$–$C_4$-alkyl)—CO—OR$^8$, —CH═N—OR$^{13}$, —C($R^{14}$)═N—OR$^{13}$, —CH(—Y—$R^{15}$, —Z—$R^{15}$), —C($R^{14}$)(—Y—$R^{15}$, —Z—$R^{15}$),

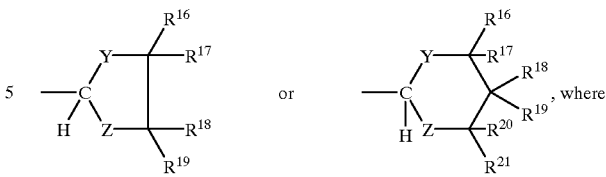

$R^8$ is hydrogen, $C_1$–$C_8$-alkyl, $C_3$–$C_8$-cycloalkyl, $C_1$–$C_8$-haloalkyl, cyano-$C_1$–$C_8$-alkyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfinyl-$C_1$–$C_4$-alkyl, $C_1$–$C_4$-alkylsulfonyl-$C_1$–$C_4$-alkyl, $C_3$–$C_8$-alkenyl, $C_5$–$C_8$-cycloalkenyl, $C_3$–$C_8$-haloalkenyl, $C_3$–$C_8$-alkynyl, hydroxycarbonyl-$C_1$–$C_4$-alkyl, ($C_1$–$C_8$-alkoxy)carbonyl-$C_1$–$C_6$-alkyl, ($C_3$–$C_8$-alkenyloxy)carbonyl-$C_1$–$C_6$-alkyl, ($C_3$–$C_8$-alkynyloxy)carbonyl-$C_1$–$C_6$-alkyl, $C_1$–$C_4$-alkoxy-($C_1$–$C_4$-alkoxy)carbonyl-$C_1$–$C_4$-alkyl, ($C_1$–$C_8$-haloalkoxy)carbonyl-$C_1$–$C_6$-alkyl, $C_3$–$C_8$-cycloalkyloxy)carbonyl-$C_1$–$C_6$-alkyl, ($C_1$–$C_4$-alkoxy)carbonyl-($C_1$–$C_4$-alkoxy)carbonyl-$C_1$–$C_4$-alkyl, ($C_3$–$C_6$-alkenyloxy)carbonyl-$C_1$–$C_4$-alkoxy)carbonyl-$C_1$–$C_4$-alkyl, ($C_3$–$C_6$-alkynyloxy)carbonyl-($C_1$–$C_4$-alkoxy)carbonyl-$C_1$–$C_4$-alkyl, hydroxycarbonyl-($C_1$–$C_4$-alkoxy)carbonyl-$C_1$–$C_4$-alkyl, oxetan-3-yloxycarbonyl-$C_1$–$C_4$-alkyl, phenoxycarbonyl-$C_1$–$C_4$-alkyl, benzyl or benzyloxycarbonyl-$C_1$–$C_4$-alkyl, where each of the phenyl rings of the last 3 radicals may be unsubstituted or may carry one to three substituents, in each case selected from the group consisting of nitro, cyano, hydroxyl, hydroxycarbonyl, halogen, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkoxy)carbonyl and ($C_1$–$C_4$-alkoxy)carbonyl-$C_1$–$C_4$-alkoxy;

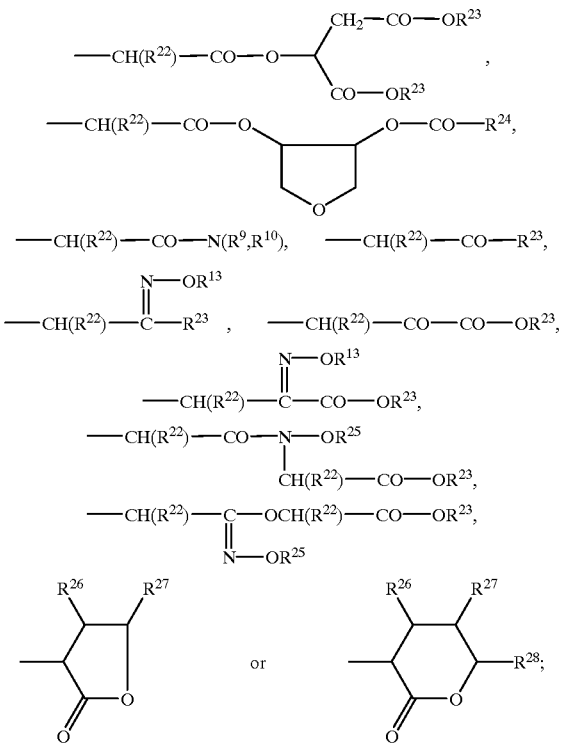

$R^9$ and $R^{10}$ independently of one another are each hydrogen, $C_1$–$C_8$-alkyl, $C_3$–$C_8$-cycloalkyl, $C_3$–$C_8$- alkenyl, $C_3$–$C_8$-alkynyl, $C_1$–$C_8$-haloalkyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfinyl-$C_1$–$C_4$-alkyl, $C_1$–$C_4$-alkylsulfonyl-$C_1$–$C_4$-alkyl, cyano-$C_1$–$C_8$-alkyl, hydroxycarbonyl-$C_1$–$C_4$-alkyl, ($C_1$–$C_4$-alkoxy) carbonyl-$C_1$–$C_4$-alkyl, ($C_3$–$C_7$-cycloalkyloxy) carbonyl-$C_1$–$C_4$-alkyl, ($C_1$–$C_4$-alkoxy)carbonyl-$C_3$–$C_7$-cycloalkyl, $C_1$–$C_4$-alkoxy-($C_1$–$C_4$-alkoxy) carbonyl-$C_1$–$C_4$-alkyl, $C_1$–$C_6$-alkoxy, phenyl or phenyl-$C_1$–$C_4$-alkyl, where the phenyl rings of the last two radicals may be unsubstituted or may carry one to three substituents, in each case selected from the group consisting of nitro, cyano, hydroxyl, halogen, $C_1$–$C_4$-haloalkyl, $C_1$–$C_4$-alkoxy, $C_1$–$C_4$-haloalkoxy, ($C_1$–$C_4$-alkoxy)carbonyl and ($C_1$–$C_4$-alkoxy)carbonyl-$C_1$–$C_4$-alkoxy;

or $R^9$ and $R^{10}$ together are a tetramethylene, pentamethylene or ethyleneoxyethylene chain, each of which may carry a hydroxycarbonyl group or a ($C_1$–$C_6$-alkoxy) carbonyl radical;

$R^{11}$ is hydrogen, $C_1$–$C_8$-alkyl, $C_3$–$C_8$-alkenyl or $C_3$–$C_8$-alkynyl;

$R^{12}$ and $R^{13}$ independently of one another are each hydrogen, $C_1$–$C_8$-alkyl, $C_3$–$C_8$-alkenyl, $C_3$–$C_8$-alkynyl, $C_1$–$C_8$-haloalkyl, $C_1$–$C_4$-alkoxy-$C_1$–$C_4$-alkyl, ($C_1$–$C_4$-alkoxy)carbonyl-$C_1$–$C_4$-alkyl, $C_3$–$C_8$-cycloalkyl, phenyl or phenyl-$C_1$–$C_4$-alkyl, where the phenyl rings of the last two radicals may be unsubstituted or may carry one to three substituents, in each case selected from the group consisting of nitro, cyano, hydroxyl, hydroxycarbonyl, halogen, $C_1$–$C_4$-haloalkyl, $C_1$–$C_4$-alkoxy, $C_1$–$C_4$-haloalkoxy, ($C_1$–$C_4$-alkoxy) carbonyl and ($C_1$–$C_4$-alkoxy)carbonyl-$C_1$–$C_4$-alkoxy;

$R^{14}$ is $C_1$–$C_8$-alkyl;

Y and Z independently of one another are each oxygen or sulfur;

$R^{15}$ is $C_1$–$C_8$-alkyl, $C_1$–$C_8$-haloalkyl or $C_1$–$C_4$-alkoxy-$C_1$–$C_4$-alkyl;

$R^{16}$–$R^{21}$ independently of one another are each hydrogen, cyano, $C_1$–$C_8$-alkyl, $C_1$–$C_4$-alkoxy-$C_1$–$C_4$-alkyl, $C_1$–$C_8$-alkoxy, $C_1$–$C_4$-alkoxy-$C_1$–$C_4$-alkoxy, hydroxycarbonyl, ($C_1$–$C_8$-alkoxy)carbonyl, aminocarbonyl, ($C_1$–$C_8$-alkyl)aminocarbonyl or di($C_1$–$C_8$-alkyl)aminocarbonyl;

$R^{22}$–$R^{25}$ independently of one another are each hydrogen, $C_1$–$C_8$-alkyl, $C_1$–$C_4$-alkoxy-$C_1$–$C_4$-alkyl, $C_3$–$C_8$-alkenyl or $C_3$–$C_8$-alkynyl and $R^{26}$–$R^{28}$ independently of one another are each hydrogen or $C_1$–$C_8$-alkyl;

$R^6$ is hydrogen, nitro, halogen, —$OR^{29}$ or —CO—$OR^{29}$ and $R^7$ is hydrogen, nitro, halogen or —$OR^{30}$, where $R^{29}$ and $R^{30}$ each have one of the meanings of $R^8$, and the agriculturally useful salts of the compounds I, except for those compounds I, where X is methylene and $R^5$ is —$OR^8$ and $R^3$ and $R^7$ are both hydrogen or $R^1$ is halogen and $R^3$, $R^4$, $R^6$ and $R^7$ are all simultaneously hydrogen.

Furthermore, the invention relates to the use of the compounds I as herbicides or for the dessication/defoliation of plants, herbicidal compositions and compositions for the dessication and/or defoliation of plants which comprise compounds I as active ingredients, methods for controlling undesirable vegetation and for the dessication and/or defoliation of plants using the compounds I and processes for preparing the compounds I and the herbicidal compositions and compositions for the dessication and/or defoliation of plants using the compounds I.

EP-A 047 972 describes phenoxyalkanoic acid derivatives for increasing the carbohydrate depositing in plants whose general formula—if the variables are appropriately chosen—also includes compounds I where n=0, X methylene, $R^1$=halogen, di- or trifluoromethyl, $R^2$=fluorine or chlorine, $R^3$, $R^4$, $R^6$ and $R^7$=hydrogen and $R^5$=ethoxy, 2-butoxy or but-3-en-2-yloxy, in each case substituted with a hydroxycarbonyl radical or certain ester, thioester or carboxamide radicals.

Those 2-benzylpyridines I where n=0, X=methylene, $R^1$=halogen or trifluoromethyl, $R^3$, $R^4$ and $R^7$=hydrogen, $R^5$=ethoxy, 2-butoxy or but-3-en-2-yloxy, each of which carries a certain carboxamide group, and $R^6$=hydrogen or halogen are included in the general formula of the herbicides and fungicides disclosed in DE-A 29 48 095.

The Swiss Patent CH 642 075 discloses a compound where n=0, X=methylene, $R^1$=chlorine, $R^2$=hydrogen, $R^3$, $R^4$, $R^6$ and $R^7$=hydrogen and $R^5$=2-(ethoxycarbonyl)but-2-yloxy which is said to have pharmaceutical activity.

Benz(o)ylpyridines of the type of the compounds I are also included in the general formulae of the herbicides described in WO 92/22203, EP-A 078 536 and EP-A 461 079.

The two benzylpyridines

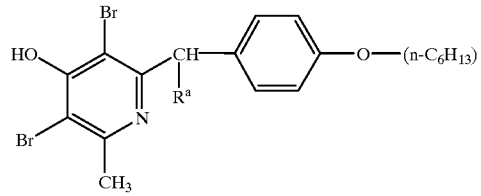

where $R^a$=H (No. 20) or $OC_2H_5$ (No. 21) are known as inhibitors of photosynthesis from T. Asami et al., Biosci. Biotech. Biochem. 57(2) (1993), 350/351.

Finally, WO 96/17829 discloses certain herbicidal 3-benzoylpyridines.

The herbicidal properties of the abovementioned herbicides are, with a view to the harmful plants, not always entirely satisfactory.

It is an object of the present invention, therefore, to provide novel herbicidally active compounds which allow better selective control of undesirable plants than known compounds. It is a further object to provide novel compounds which have a dessicant/defoliant action.

We have found that these objects are achieved by the present substituted 2-benz(o)ylpyridines of the formula I and by their herbicidal action.

Furthermore, we have found herbicidal compositions which comprise the compounds I and have very good herbicidal activity. Moreover, we have found processes for preparing these compositions and methods for controlling undesirable vegetation using the compounds I.

Furthermore, we have found that the compounds I are also suitable for the dessication/defoliation of parts of plants, suitable plants being crop plants such as cotton, potatoes, oilseed rape, sunflower, soybean or field beans, in particular cotton. In this regard, we have found compositions for the dessication and/or defoliation of plants, processes for preparing these compositions and methods for the dessication and/or defoliation of plants using the compounds I.

Depending on the substitution pattern, the compounds of the formula I can contain one or more chiral centers, in which case they exist in the form of enantiomer or diastereomer mixtures. E/Z isomers are also possible provided that at least one substituent with a double bond is present. This invention provides the pure enantiomers or diastereomers and mixtures thereof.

Agriculturally useful salts are in particular the salts of I with those cations and the acid addition salts of I with those acids which do not adversely affect the herbicidal or dessicant/defoliant activity of I.

Suitable cations are therefore in particular the ions of the alkali metals, preferably sodium and potassium, of the alkaline earth metals, preferably calcium, magnesium and barium, and of the transition metals, preferably manganese, copper, zinc and iron, and the ammonium ion, which may carry one $C_1$–$C_4$-alkyl, phenyl or benzyl substituent and, if desired, additionally one to three further $C_1$–$C_4$-alkyl radicals, preferably diisopropylammonium, tetramethylammonium, tetrabutylammonium, trimethylbenzylammonium, and furthermore phosphonium ions, preferably tri($C_1$–$C_4$-alkyl)phosphonium, sulfonium ions, preferably tri($C_1$–$C_4$-alkyl)sulfonium, and sulfoxonium ions, preferably tri-($C_1$–$C_4$-alkyl)sulfoxonium.

Anions of useful acid addition salts are primarily fluoride, chloride, bromide, hydrogensulfate, sulfate, dihydrogenphosphate, hydrogenphosphate, phosphate, nitrate, hydrogencarbonate, carbonate, hexafluorosilicate, hexafluorophosphate, benzoate, oxalate, dodecylbenzenesulfonate, and the anions of $C_1$–$C_4$-alkanoic acid, preferably formate, acetate, propionate and butyrate.

The organic molecular moieties mentioned for the substituents $R^1$, $R^3$, $R^4$, $R^5$ and $R^8$ to $R^{30}$ or as radicals on phenyl rings are collective terms for individual listings of the individual group members. All hydrocarbon chains, ie. all the alkyl, haloalkyl, cyanoalkyl, oxetanyloxycarbonylalkyl, hydroxycarbonylalkyl, phenylalkyl, phenoxycarbonylalkyl, benzyloxycarbonylalkyl, alkoxy, haloalkoxy, alkylthio, alkylsulfinyl, alkylsulfonyl, alkenyl, haloalkenyl, cyanoalkenyl, alkenyloxy, alkynyl, haloalkynyl, cyanoalkynyl and alkynyloxy moieties can be straight-chain or branched. Halogenated substituents preferably carry one to five identical or different halogen atoms.

The term halogen represents in each case fluorine, bromine, chlorine or iodine, in particular fluorine or chlorine.

Other examples of meanings are for:

$C_1$–$C_4$-alkyl: $CH_3$, $C_2H_5$, $CH_2$–$C_2H_5$, $CH(CH_3)_2$, n-$C_4H_9$, $CH(CH_3)$—$C_2H_5$, $CH_2$—$CH(CH_3)_2$ or $C(CH_3)_3$, in particular $CH_3$ or $C_2H_5$;

$C_1$–$C_4$-haloalkyl: a $C_1$–$C_4$-alkyl radical as mentioned above which is partially or fully substituted by fluorine, chlorine, bromine and/or iodine, ie. for example $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, $CH_2$—$CHF_2$, $CH_2$–$CF_3$, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular $CH_2F$, $CHF_2$, $CF_3$, $CH_2Cl$, 2-fluoroethyl, 2-chloroethyl or $CH_2$—$CF_3$;

$C_1$–$C_8$-alkyl: $C_1$–$C_4$-alkyl as mentioned above, or, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, $CH_2$—$C_2H_5$, $CH(CH_3)_2$, n-butyl, $C(CH_3)_3$, n-pentyl or n-hexyl;

$C_1$–$C_8$-haloalkyl: a $C_1$–$C_8$-alkyl radical as mentioned above which is partially or fully substituted by fluorine, chlorine, bromine and/or iodine, ie. for example one of the radicals mentioned for $C_1$–$C_4$-haloalkyl, or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular $CH_2F$, $CHF_2$, $CF_3$, $CH_2Cl$, 2-fluoroethyl, 2-chloroethyl or $CH_2$—$CF_3$;

cyano-$C_1$–$C_8$-alkyl: for example $CH_2CN$, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-cyano-2-methylprop-3-yl, 2-cyano-2-methylprop-3-yl, 3-cyano-2-methylprop-3-yl, 2-($CH_2CN$)prop-2-yl or 2-cyanohex-6-yl, in particular $CH_2CN$ or 2-cyanoethyl;

oxetan-3-yloxycarbonyl-$C_1$–$C_4$-alkyl: for example oxetan-3-yloxycarbonylmethyl, 2-(oxetan-3-yloxycarbonyl)ethyl, 2-(oxetan-3-yloxycarbonyl)prop-1-yl, 3-(oxetan-3-yloxycarbonyl)prop-1-yl, 2-(oxetan-3-yloxycarbonyl)but-1-yl, 3-(oxetan-3-yloxycarbonyl)but-1-yl, 4-(oxetan-3-yloxycarbonyl)but-1-yl, 1-(oxetan-3-yloxycarbonyl)but-2-yl, 3-(oxetan-3-yloxycarbonyl)but-2-yl, 4-(oxetan-3-yloxycarbonyl)but-2-yl, 1-(oxetan-3-yloxycarbonylmethyl)eth-1-yl, 1-(oxetan-3-yloxycarbonylmethyl)-1-(methyl)eth-1-yl or 1-(oxetan-3-yloxycarbonylmethyl)prop-1-yl, in particular oxetan-3-yloxycarbonylmethyl or 2-(oxetan-3-yloxycarbonyl)ethyl;

hydroxycarbonyl-$C_1$–$C_4$-alkyl: $CH_2COOH$, $CH(CH_3)COOH$, 2-(COOH)ethyl, 1-(COOH)prop-1-yl, 2-(COOH)prop-1-yl, 3-(COOH)prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)eth-1-yl or 1-($CH_2COOH$)prop-1-yl, in particular $CH_2COOH$ or 2-(COOH)ethyl;

hydroxycarbonyl-$C_1$–$C_8$-alkyl: hydroxycarbonyl-$C_1$–$C_4$-alkyl as mentioned above, and, for example, 5-(COOH)pent-1-yl or 6-(COOH)hex-1-yl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2- yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl or 1-(phenylmethyl)prop-1-yl, in particular benzyl or 2-phenylethyl;

phenoxycarbonyl-$C_1$–$C_4$-alkyl: phenoxycarbonylmethyl, 1-(phenoxycarbonyl)ethyl, 2-(phenoxycarbonyl)ethyl, 1-(phenoxycarbonyl)prop-1-yl, 2-(phenoxycarbonyl)prop-1-yl, 3-(phenoxycarbonyl)prop-1-yl, 1-(phenoxycarbonyl)but-1-yl, 2-(phenoxycarbonyl)but-1-yl, 3-(phenoxycarbonyl)but-1-yl, 4-(phenoxycarbonyl)but-1-yl, 1-(phenoxycarbonyl)but-2-yl, 2-(phenoxycarbonyl)but-2-yl, 3-(phenoxycarbonyl)but-2-yl, 4-(phenoxycarbonyl)but-2-yl, 1-(phenoxycarbonylmethyl)eth-1-yl, 1-(phenoxycarbonylmethyl)-1-(methyl)eth-1-yl or 1-(phenoxycarbonylmethyl)prop-1-yl, in particular phenoxycarbonylmethyl or 2-(phenoxycarbonyl)ethyl;

benzyloxycarbonyl-$C_1$–$C_4$-alkyl: benzyloxycarbonylmethyl, 1-(benzyloxycarbonyl)ethyl, 2-(benzyloxycarbonyl)ethyl, 1-(benzyloxycarbonyl)prop-1-yl, 2-(benzyloxycarbonyl)prop-1-yl, 3-(benzyloxycarbonyl)prop-1-yl, 1-(benzyloxycarbonyl)but-1-yl, 2-(benzyloxycarbonyl)but-1-yl, 3-(benzyloxycarbonyl)but-1-yl, 4-(benzyloxycarbonyl)but-1-yl, 1-(benzyloxycarbonyl)but-2-yl, 2-(benzyloxycarbonyl)but-2-yl, 3-(benzyloxycarbonyl)but-2-yl, 4-(benzyloxycarbonyl)but-2-yl, 1-(benzyloxycarbonylmethyl)eth-1-yl, 1-(benzyloxycarbonylmethyl)-1-(methyl)eth-1-yl or 1-(benzyloxycarbonylmethyl)prop-1-yl, in particular benzyloxycarbonylmethyl or 2-(benzyloxycarbonyl)ethyl;

$C_1$–$C_4$-alkoxy: $OCH_3$, $OC_2H_5$, n-propoxy, $OCH(CH_3)_2$, n-butoxy, 1-methylpropoxy, $OCH_2$—$CH(CH_3)_2$ or $OC(CH_3)_3$, in particular $OCH_3$ or $OC_2H_5$;

$C_1$–$C_6$-alkoxy: a $C_1$–$C_4$-alkoxy radical as mentioned above, or, for example, n-pentoxy, 1-methylbutoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular $OCH_3$, $OC_2H_5$, $OCH_2$—$C_2H_5$, $OCH(CH_3)_2$, n-butoxy, $OC(CH_3)_3$, n-pentoxy or n-hexoxy;

$C_1$–$C_8$-alkoxy; a $C_1$–$C_6$-alkoxy radical as mentioned above, or, for example, $O(n-C_7H_{15})$ or $O(n-C_8H_{17})$, in particular $C_1$–$C_6$-alkoxy;

$C_1$–$C_4$-haloalkoxy: a $C_1$–$C_4$-alkoxy radical as mentioned above which is partially or fully substituted by fluorine, chlorine, bromine and/or iodine, ie. for example $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, $OCH_2$—$CHF_2$, $OCH_2$—$CF_3$, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2H_5$, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or $n-C_4F_9$, in particular 2-chloroethoxy or $OCH_2$—$CF_3$;

($C_1$–$C_4$-alkoxy)carbonyl: CO—$OCH_3$, CO—$OC_2H_5$, CO—$OCH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$ or CO—$OC(CH_3)_3$, in particular CO—$OCH_3$ or CO—$OC_2H_5$;

($C_1$–$C_6$-alkoxy)carbonyl: a ($C_1$–$C_4$-alkoxy)carbonyl radical as mentioned above, or, for example, (n-pentoxy)carbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, (n-hexoxy)carbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular $COOCH_3$, $COOC_2H_5$, n-propoxycarbonyl, $COOCH(CH_3)_2$, n-butoxycarbonyl, $COOC(CH_3)_3$, n-pentoxycarbonyl or n-hexoxycarbonyl;

($C_1$–$C_8$-alkoxy)carbonyl: a ($C_1$–$C_6$-alkoxy)carbonyl radical as mentioned above, or, for example, CO—$O(n-C_7H_{15})$ or CO—$O(n-C_8H_{17})$, in particular ($C_1$–$C_6$-alkoxy)carbonyl;

$C_1$–$C_4$-alkylthio: $SCH_3$, $SC_2H_5$, $SCH_2$—$C_2H_5$, $SCH(CH_3)_2$, n-butylthio, $SCH(CH_3)$—$C_2H_5$, $SCH_2$—$CH(CH_3)_2$ or $SC(CH_3)_3$, in particular $SCH_3$ or $SC_2H_5$;

—$C_1$–$C_4$-alkoxy-$C_1$–$C_4$-alkyl: $C_1$–$C_4$-alkyl which is substituted by $C_1$–$C_4$-alkoxy as mentioned above, ie. for example $CH_2$—$OCH_3$, $CH_2$—$OC_2H_5$, $CH_2$—$OCH_2$—$C_2H_5$, $CH_2$—$OCH(CH_3)_2$, n-butoxymethyl, (1-methylpropoxy)methyl, (2-methylpropoxy)methyl, $CH_2$—$OC(CH_3)_2$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)

butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular $CH_2$—$OCH_3$ or 2-methoxyethyl;

$C_1$–$C_4$-alkoxy-$C_1$–$C_4$-alkoxy: $C_1$–$C_4$-alkoxy which is substituted by $C_1$–$C_4$-alkoxy as mentioned above, je. for example $OCH_2$—$OCH_3$, $OCH_2$—$OC_2H_5$, $OCH_2$—$OCH_2$—$C_2H_5$, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-mnethylethoxy)butoxy, 4-(n-butoxy)butoxy, 4-(1-methyipropoxy)butoxy, 4-(2-methylpropoxy)butoxy or 4-(1,1-dimethylethoxy)butoxy, in particular $OCH_2$—$OCH_3$ or 2-methoxyethoxy;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, ie. for example $CH_2COOCH_3$, $CH_2COOC_2H_5$, $CH(CH_3)COOCH_3$ or 2-(COOCH$_3$) ethyl;

($C_1$–$C_4$-alkoxy)carbonyl-$C_1$–$C_6$-alkyl: $C_1$–$C_6$-alkyl which is substituted by ($C_1$–$C_8$-alkoxy)carbonyl as mentioned above, ie. for example $CH_2COOCH_3$, $CH_2COOC_2H_5$, $CH(CH_3)COOCH_3$, $CH(CH_3)COOC_2H_5$, $C(CH_3)_2COOCH_3$ or $C(CH_3)_2COOC_2H_5$;

hydroxycarbonyl-($C_1$–$C_4$-alkoxy) carbonyl-$C_1$–$C_4$-alkyl: ($C_1$–$C_4$-alkoxy)carbonyl-$C_1$–$C_4$-alkyl as mentioned above which carries a hydroxycarbonyl group, ie. for example $CH_2$—$COOCH_2$—COOH, $CH(CH_3)$—$COOCH_2$—COOH, $CH_2$—$COOCH(CH_3)$—COOH or $CH(CH_3)$—$COOCH(CH_3)$—COOH;

$C_1$–$C_4$-alkoxy-($C_1$–$C_4$-alkoxy)carbonyl-$C_1$–$C_4$-alkyl: ($C_1$–$C_4$-alkoxy)carbonyl-$C_1$–$C_4$-alkyl as mentioned above which carries a $C_1$–$C_4$-alkoxy group such as $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ and $OC(CH_3)_3$, ie. for example $CH_2$—$COOCH_2$—$OCH_3$, $CH_2$—$COOCH_2$—$OC_2H_5$, $CH_2$—$COOCH_2$—OCH($CH_3)_2$, $CH_2$—$COOCH_2$—$OC(CH_3)_3$, $CH_2$—$COOCH_2$—$CH_2$—$OCH_3$, $CH_2$—$COOCH_2$—$CH_2$—$OC_2H_5$, $CH(CH_3)$—$COOCH_2$—$CH_2$—$OCH_3$ or $CH(CH_3)$—$COOCH_2$—$CH_2$—$OC_2H_5$, in particular $CH_2$—$COOCH_2$—$CH_2$—OCH3, $CH_2$—$COOCH_2$—$CH_2$—$OC_2H_5$, $CH(CH_3)$—$COOCH_2$—$CH_2$—$OCH_3$ or $CH(CH_3)$—$COOCH_2$—$CH_2$—$OC_2H_5$;

($C_1$–$C_4$-alkoxy)carbonyl-($C_1$–$C_4$-alkoxy)carbonyl-$C_1$–$C_4$-alkyl: ($C_1$–$C_4$-alkoxy)carbonyl-$C_1$–$C_4$-alkyl as mentioned above which carries a ($C_1$–$C_4$-alkoxy) carbonyl group such as $COOCH_3$, $COOC_2H_5$, $COOCH_2$—$C_2H_5$, $COOCH(CH_3)_2$, $COOCH_2$—(n-$C_3H_7$), $OCH(CH_3)$—$C_2H_5$, $OCH_2$—$CH(CH_3)_2$ and $OC(CH_3)_3$, ie. for example $CH_2$—$COOCH_2$—$COOCH_3$, $CH_2$—$COOCH_2$—$COOC_2H_5$, $CH_2$—$COOCH_2$—$COOCH(CH_3)_2$, $CH_2$—$COOCH_2$—$COOC(CH_3)_3$, $CH_2$—$COOCH_2$—$COOCH_3$, $CH_2$—$COOCH_2$—$COOC_2H_5$, $CH(CH_3)$—$COOCH_2$—$COOCH_3$, $CH(CH_3)$—$COOCH_2$—$COOC_2H_5$, $CH_2$—$COOCH(CH_3)$—$COOCH_3$, $CH_2$—$COOCH(CH_3)$—$COOC_2H_5$, $CH(CH_3)$—$COOCH(CH_3)$—$COOCH_3$ or $CH(CH_3)$—$COOCH(CH_3)$—$COOC_2H_5$, in particular $CH_2$—$COOCH_2$—$COOCH_3$, $CH_2$—$COOCH_2$—$COOC_2H_5$, $CH(CH_3)$—$COOCH_2$—$COOCH_3$, $CH(CH_3)$—$COOCH_2$—$COOC_2H_5$, $CH_2$—$COOCH(CH_3)$—$COOCH_3$, $CH_2$—$COOCH(CH_3)$—$COOC_2H_5$, $CH(CH_3)$—$COOCH(CH_3)$—$COOCH_3$ or $CH(CH_3)$—$COOCH(CH_3)$—$COOC_2H_5$;

($C_1$–$C_8$-haloalkoxy)carbonyl-$C_1$–$C_6$-alkyl: $C_1$–$C_6$-alkyl which is substituted by ($C_1$–$C_8$-haloalkoxy)carbonyl such as $COOCH_2F$, $COOCHF_2$, $COOCF_3$, $COOCH_2Cl$, $COOCH(Cl)_2$, $COOC(Cl)_3$, $COOCHFCl$, $COOCF(Cl)_2$, $COOCF_2Cl$, $COOCF_2Br$, $COOCHF$—$CH_3$, $COOCH_2$—$CH_2F$, $COOCH_2$—$CH_2Cl$, $COOCH_2$—$CH_2Br$, $COOCH_2$—$CH_2I$, $COOCH_2$—$CH_2F$, $COOCH_2$—$CF_3$, $COOCH_2$—$CHFCl$, $COOCH_2$—$CF_2Cl$, $COOCH_2$—$CF(Cl)_2$, $COOCH_2$—$C(Cl)_3$, $COOC_2F_5$, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, $COOCH_2CH_2$—$CF_3$, $COOCH_2CH_2$—$C(Cl)_3$, $COOCH_2$—$C_2F_5$, $COOCF_2$—$C_2F_5$, 1-($CH_2F$)-2-fluoroethoxycarbonyl, 1-($OCH_2Cl$)-2-chloroethoxycarbonyl, 1-($OCH_2Br$)-2-bromoethoxycarbonyl, 4-fluorobutoxycarbonyl, 4-chlorobutoxycarbonyl, 4-bromobutoxycarbonyl, $COOCF_2CF_2$—$C_2F_5$, 5-fluoropentoxycarbonyl, 5-chloropentoxycarbonyl, 5-bromopentoxycarbonyl, 5-iodopentoxycarbonyl, 5,5,5-trichloropentoxycarbonyl, $COOCF_2$—(n-$C_4F_9$), 6-fluorohexoxycarbonyl, 6-chlorohexoxycarbonyl, 6-bromohexoxycarbonyl, 6-iodohexoxycarbonyl, 6,6,6-trichlorohexoxycarbonyl and $COOCF_2$—(n-$C_5F_{11}$), ie. for example $CH_2$—$COOCH_2$—$CF_3$, $CH(CH_3)$—$COOCH_2$—$CF_3$, $CH_2$—$COOCH_2$—$C(Cl)_3$ or $CH(CH_3)$—$COOCH_2$—$C(Cl)_3$;

($C_1$–$C_4$-alkoxy)carbonyl-$C_1$–$C_4$-alkoxy: $C_1$–$C_4$-alkoxy, which is substituted by ($C_1$–$C_4$-alkoxy)carbonyl as mentioned above, ie. for example $OCH_2COOCH_3$, $OCH_2COOC_2H_5$, $OCH_2COOCH_2$—$C_2H_5$, $OCH_2COOCH(CH_3)_2$, $OCH_2COOCH_2CH_2$—$C_2H_5$, $OCH_2COOCH(CH_3)$—$C_2H_5$, $OCH_2COOCH_2$—CH($CH_3)_2$, $OCH_2COOC(CH_3)_3$, $OCH(CH_3)COOCH_3$, $OCH(CH_3)COOC_2H_5$, $OCH_2CH_2COOCH_3$, $OCH_2CH_2COOC_2H_5$, $OCH_2CH_2COOCH_2$—$C_2H_5$, $OCH_2CH_2COOCH(CH_3)_2$, $OCH_2CH_2COOCH_2CH_2$—$CH_2H_5$, 2-[COOCH($CH_3)$—$C_2H_5$]ethoxy, 2-[$COOCH_2$—CH($CH_3)_2$] ethoxy, $OCH_2CH_2COOC(CH_3)_3$, 2-($COOCH_3$) propoxy, 2-($COOC_2H_5$)propoxy, 2-($COOCH_2$—$C_2H_5$) propoxy, 2-[$COOCH(CH_3)_2$]propoxy, 2-(COOCH$_2$CH$_2$—C$_2$H$_5$)propoxy, 2-[COOCH(CH$_3$)—C$_2$H$_5$]propoxy, 2-[COOCH$_2$—CH(CH$_3$)$_2$]propoxy, 2-[COOC(CH$_3$)$_3$]propoxy, 3-(COOCH$_3$)propoxy, 3-(COOC$_2$H$_5$)propoxy, 3-(COOCH$_2$—C$_2$H$_5$)propoxy, 3-[COOCH(CH$_3$)$_2$]propoxy, 3-(COOCH$_2$CH$_2$—C$_2$H$_5$)propoxy, 3-[COOCH(CH$_3$)—C$_2$H$_5$]-propoxy, 3-[COOCH$_2$—CH(CH$_3$)$_2$]propoxy, 3-[COOC(CH$_3$)$_3$]propoxy, 2-(COOCH$_3$)butoxy, 2-(COOC$_2$H$_5$)butoxy, 2-(COOCH$_2$—C$_2$H$_5$)butoxy, 2-[COOCH(CH$_3$)$_2$]butoxy, 2-(COOCH$_2$CH$_2$—C$_2$H$_5$)butoxy, 2-[COOCH(CH$_3$)—C$_2$H$_5$]]butoxy, 2-[COOCH$_2$—CH(CH$_3$)$_2$]butoxy, 2-[COOC(CH$_3$)$_3$]butoxy, 3-(COOCH$_3$)butoxy, 3-(COOC$_2$H$_5$)butoxy, 3-(COOCH$_2$—C$_2$H$_5$)butoxy, 3-[COOCH(CH$_3$)$_2$]butoxy, 3-(COOCH$_2$CH$_2$—C$_2$H$_5$)butoxy, 3-[COOCH(CH$_3$)—C$_2$H$_5$]butoxy, 3-[COOCH$_2$—CH(CH$_3$)$_2$]butoxy, 3-[COOC(CH$_3$)$_3$]butoxy, 4-(COOCH$_3$)butoxy, 4-(COOC$_2$H$_5$)butoxy, 4-(COOCH$_2$—C$_2$H$_5$)butoxy, 4-[COOCH(CH$_3$)$_2$]butoxy, 4-(COOCH$_2$CH$_2$—C$_2$H$_5$)butoxy, 4-[COOCH(CH$_3$)—C$_2$H$_5$]butoxy, 4-[COOCH$_2$—CH(CH$_3$)$_2$]butoxy or 4-[1,1-COOC(CH$_3$)$_3$]butoxy, in particular OCH$_2$—COOCH$_3$, OCH$_2$—COOC$_2$H$_5$, OCH$_2$—COOCH$_2$—C$_2$H$_5$, OCH$_2$—COOCH(CH$_3$)$_2$, OCH$_2$—COOCH$_2$—CH$_2$—C$_2$H$_5$, OCH$_2$—COOCH(CH$_3$)—C$_2$H$_5$, OCH$_2$—COOCH$_2$—CH(CH$_3$)$_2$, OCH$_2$—COOCH$_2$—CH$_2$CH$_2$—C$_2$H$_5$, OCH(CH$_3$)—COOCH$_3$, OCH(CH$_3$)—COOC$_2$H$_5$, OCH(CH$_3$)—COOCH$_2$—C$_2$H$_5$, OCH(CH$_3$)—COOCH(CH$_3$)$_2$, OCH(CH$_3$)—COOCH$_2$—CH$_2$—C$_2$H$_5$, OCH(CH$_3$)—COOCH(CH$_3$)—C$_2$H$_5$, OCH(CH$_3$)—COOCH$_2$—CH(CH$_3$)$_2$, OCH(CH$_3$)—COOC(CH$_3$)$_3$ or OCH(CH$_3$)—COOCH$_2$—CH$_2$CH$_2$—C$_2$H$_5$;

C$_1$–C$_4$-alkylthio-C$_1$–C$_4$-alkyl: C$_1$–C$_4$-alkyl which is substituted by C$_1$–C$_4$-alkylthio as mentioned above, ie. for example CH$_2$—SCH$_3$, CH$_2$—SC$_2$H$_5$, n-propylthiomethyl, CH$_2$—SCH(CH$_3$)$_2$, n-butylthiomethyl, (1-methylpropylthio)methyl, (2-methylpropylthio)methyl, CH$_2$—SC(CH$_3$)$_3$, 2-methylthioethyl, 2-ethylthioethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 3-(methylthio)propyl, 2-(ethylthio)propyl, 3-(ethylthio)propyl, 3-(propylthio)propyl, 3-(butylthio)propyl, 4-(methylthio)butyl, 4-(ethylthio)butyl, 4-(n-propylthio)butyl or 4-(n-butylthio)butyl, in particular 2-(methylthio)ethyl;

C$_1$–C$_4$-alkylsulfinyl: SO—CH$_3$, SOC$_2$H$_5$, SO—CH$_2$—C$_2$H$_5$, SO—CH(CH$_3$)$_2$, n-butylsulfinyl, 1-methylpropylsulfinyl, 2-methylpropylsulfinyl or SO—C(CH$_3$)$_3$, in particular SO—CH$_3$ or SO—C$_2$H$_5$;

C$_1$–C$_4$-alkylsulfinyl-C$_1$–C$_4$-alkyl: C$_1$–C$_4$-alkyl which is substituted by C$_1$–C$_4$-alkylsulfinyl as mentioned above, preferably by SO—CH$_3$, ie. for example CH$_2$—SO—CH$_3$ or 2-methylsulfinylethyl;

C$_1$–C$_4$-alkylsulfonyl: SO$_2$—CH$_3$, SO$_2$—C$_2$H$_5$, SO$_2$—CH$_2$—C$_2$H$_5$, SO$_2$—CH(CH$_3$)$_2$, n-butylsulfonyl, 1-methylpropylsulfonyl, SO$_2$—CH$_2$—CH(CH$_3$)$_2$ or SO$_2$—C(CH$_3$)$_3$, in particular SO$_2$—CH$_3$ or SO$_2$—C$_2$H$_5$;

C$_1$–C$_4$-alkylsulfonyl-C$_1$–C$_4$-alkyl: C$_1$–C$_4$-alkyl which is substituted by C$_1$–C$_4$-alkylsulfonyl as mentioned above, preferably by SO$_2$—CH$_3$, ie. for example CH$_2$—SO$_2$—CH$_3$ or 2-methylsulfonylethyl;

(C$_1$–C$_8$-alkyl)aminocarbonyl: for example CO—NH—CH$_3$, CO—NH—C$_2$H$_5$, CO—NH—CH$_2$—C$_2$H$_5$, CO—NH—CH(CH$_3$)$_2$, CO—NH—CH$_2$CH$_2$—C$_2$H$_5$, CO—NH—CH(CH$_3$)C$_2$H$_5$, CO—NH—CH$_2$—CH(CH$_3$)$_2$, CO—NH—C(CH$_3$)$_3$, n-pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, n-hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, in particular CO—NH—CH$_3$, CO—NH—C$_2$H$_5$, n-propylaminocarbonyl, CO—NH—CH(CH$_3$)$_2$, n-butylaminocarbonyl, CO—NH—C(CH$_3$)$_3$, n-pentylaminocarbonyl or n-hexylaminocarbonyl;

di(C$_1$–C$_8$-alkyl)aminocarbonyl: for example CO—N(CH$_3$)$_2$, CO—N(C$_2$H$_5$)$_2$, CO—N(CH$_2$—C$_2$H$_5$)$_2$, CO—N[CH(CH$_3$)$_2$]$_2$, CO—N(n-C$_4$H$_9$)$_2$, CO—N[CH(CH$_3$)—C$_2$H$_5$]$_2$, CO—N[CH$_2$—CH(CH$_3$)$_2$]$_2$, CO—N[C(CH$_3$)$_3$]$_2$, CO—N(CH$_3$)—C$_2$H$_5$, CO—N(CH$_3$)—CH$_2$—C$_2$H$_5$, CO—N(CH$_3$)—CH(CH$_3$)$_2$, CO—N(CH$_3$)—(n-C$_4$H$_9$), CO—N(CH$_3$)—CH(CH$_3$)—C$_2$H$_5$, CO—N(CH$_3$)—CH$_2$—CH(CH$_3$)$_2$, CO—N(CH$_3$)—C(CH$_3$)$_3$, CO—N(C$_2$H$_5$)—CH$_2$—C$_2$H$_5$, CO—N(C$_2$H$_5$)—CH(CH$_3$)$_2$, CO—N(C$_2$H$_5$)—(n-C$_4$H$_9$), CO—N(C$_2$H$_5$)—CH(CH$_3$)—C$_2$H$_5$, CO—N(C$_2$H$_5$)—CH$_2$—CH(CH$_3$)$_2$, CO—N(C$_2$H$_5$)—C(CH$_3$)$_3$, N—[CH(CH$_3$)$_2$]—N-propylaminocarbonyl, N-butyl-N-propylaminocarbonyl, N—[1-methylpropyl]—N-propylaminocarbonyl, N—[2-methylpropyl]—N-propylaminocarbonyl, N—[C(CH$_3$)$_3$]—N-propylaminocarbonyl, N-butyl-N—[1-methylethyl]aminocarbonyl, N—[CH(CH$_3$)$_2$]—N—(1-methylpropyl)aminocarbonyl, N—[CH(CH$_3$)$_2$]—N—[2-methylpropyl]aminocarbonyl, N—[C(CH$_3$)$_3$]—N—[CH(CH$_3$)$_2$]aminocarbonyl, N-butyl-N—[(1-methylpropyl]aminocarbonyl, N-butyl-N—[2-methylpropyl]aminocarbonyl, N-butyl-N—[C(CH$_3$)$_3$]aminocarbonyl, N—[1-methylpropyl]—N—[2-methylpropyl]aminocarbonyl, N—[C(CH$_3$)$_3$]—N—[1-methylpropyl]aminocarbonyl or N—[C(CH$_3$)$_3$]—N—[2-methylpropyl]aminocarbonyl, in particular CO—N(CH$_3$)$_2$ or CO—N(C$_2$H$_5$)$_2$;

C$_3$–C$_8$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-2-en-1-yl, n-hept-2-en-1-yl, n-hept-3-en-1-yl, n-oct-2-en-1-yl or n-oct-3-en-1-yl, in particular prop-2-en-1-yl or n-buten-4-yl;

$C_3$–$C_8$-haloalkenyl: $C_3$–$C_6$-alkenyl as mentioned above which is partially or fully substituted by fluorine, chlorine, bromine and/or iodine, ie. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

$C_2$–$C_8$-haloalkenyl: 1-chlorovinyl, 2-chlorovinyl, 1,2-dichlorovinyl, 1,2,2-trichlorovinyl or one of the above-mentioned $C_3$–$C_8$-haloalkenyl radicals;

cyano-$C_2$–$C_8$-aikenyl: for example 2-cyanovinyl, 3-cyanoallyl, 4-cyanobut-2-enyl, 4-cyanobut-3-enyl or 5-cyanopent-4-enyl, preferably 3-cyanoallyl or 4-cyanobui-2-enyl, in particular 3-cyanoallyl;

$C_2$–$C_4$-alkenyloxy-$C_1$–$C_4$-alkyl: $C_1$–$C_4$-alkyl which is substituted by $C_2$–$C_4$-alkenyloxy such as vinyloxy, prop-2-enyloxy, but-1-en-3-yloxy, but-1-en-4-yloxy, n-but-2-enyloxy, n-but-3-enyloxy, 1-methylprop-2-enyloxy or 2-methylprop-2-enyloxy—preferably by allyloxy, 2-methylprop-2-en-1-yloxy, but-1-en-3-yloxy, but-1-en-4-yloxy or but-2-en-1-yloxy—ie. for example vinyloxymethyl, allyloxymethyl, 2-(allyloxy) ethyl or but-1-en-4-yloxymethyl;

($C_3$–$C_6$-alkenyloxy)carbonyl-($C_1$–$C_4$-alkoxy)carbonyl-$C_1$–$C_4$-alkyl: ($C_1$–$C_4$-alkoxy)carbonyl-$C_1$–$C_4$-alkyl as mentioned above which carries a ($C_3$–$C_6$-alkenyloxy) carbonyl group such as prop-1-en-1-yl-O—CO, prop-2-en-1-yl-O—CO, 1-methylethenyl-O—CO, n-buten-1-yl-O—CO, n-buten-2-yl-O—CO, n-buten-3-yl-O—CO, 1-methylprop-1-en-1-yl-O—CO, 2-methylprop-1-en-1-yl-O—CO, 1-methylprop-2-en-1-yl-O—CO, 2-methylprop-2-en-1-yl-O—CO, n-penten-1-yl-O—CO, n-penten-2-yl-O—CO, n-penten-3-yl-O—CO, n-penten-4-yl-O—CO, 1-methylbut-1-en-1-yl-O—CO, 2-methylbut-1-en-1-yl-O—CO, 3-methylbut-1-en-1-yl-O—CO, 1-methylbut-2-en-1-yl-O—CO, 2-methylbut-2-en-1-yl-O—CO, 3-methylbut-2-en-1-yl-O—CO, 1-methylbut-3-en-1-yl-O—CO, 2-methylbut-3-en-1-yl-O—CO, 3-methylbut-3-en-1-yl-O—CO, 1,1-dimethylprop-2-en-1-yl-O—CO, 1,2-dimethylprop-1-en-1-yl-O—CO, 1,2-dimethylprop-2-en-1-yl-O—CO, 1-ethylprop-1-en-1-yl-O—CO, 1-ethylprop-2-en-1-yl-O—CO, n-hex-1-en-1-yl-O—CO, n-hex-2-en-1-yl-O—CO, n-hex-3-en-1-yl-O—CO, n-hex-4-en-1-yl-O—CO, n-hex-5-en-1-yl-O—CO, 1-methylpent-1-en-1-yl-O—CO, 2-methylpent-1-en-1-yl-O—CO, 3-methylpent-1-en-1-yl-O—CO, 4-methylpent-1-en-1-yl-O—CO, 1-methylpent-2-en-1-yl-O—CO, 2-methylpent-2-en-1-yl-O—CO, 3-methylpent-2-en-1-yl-O—CO, 4-methylpent-2-en-1-yl-O—CO, 1-methylpent-3-en-1-yl-O—CO, 2-methylpent-3-en-1-yl-O—CO, 3-methylpent-3-en-1-yl-O—CO, 4-methylpent-3-en-1-yl-O—CO, 1-methylpent-4-en-1-yl-O—CO, 2-methylpent-4-en-1-yl-O—CO, 3-methylpent-4-en-1-yl-O—CO, 4-methylpent-4-en-1-yl-O—CO, 1,1-dimethylbut-2-en-1-yl-O—CO, 1,1-dimethylbut-3-en-1-yl-O—CO, 1,2-dimethylbut-1-en-1-yl-O—CO, 1,2-dimethylbut-2-en-1-yl-O—CO, 1,2-dimethylbut-3-en-1-yl-O—CO, 1,3-dimethylbut-1-en-1-yl-O—CO, 1,3-dimethylbut-2-en-1-yl-O—CO, 1,3-dimethylbut-3-en-1-yl-O—CO, 2,2-dimethylbut-3-en-1-yl-O—CO, 2,3-dimethylbut-1-en-1-yl-O—CO, 2,3-dimethylbut-2-en-1-yl-O—CO, 2,3-dimethylbut-3-en-1-yl-O—CO, 3,3-dimethylbut-1-en-1-yl-O—CO, 3,3-dimethylbut-2-en-1-yl-O—CO, 1-ethylbut-1-en-1-yl-O—CO, 1-ethylbut-2-en-1-yl-O—CO, 1-ethylbut-3-en-1-yl-O—CO, 2-ethylbut-1-en-1-yl-O—CO, 2-ethylbut-2-en-1-yl-O—CO, 2-ethylbut-3-en-1-yl-O—CO, 1,1,2-trimethylprop-2-en-1-yl-O—CO, 1-ethyl-1-methylprop-2-en-1-yl-O—CO, 1-ethyl-2-methylprop-1-en-1-yl-O—CO and 1-ethyl-2-methylprop-2-en-1-yl-O—CO, ie. for example $CH_2$—$COOCH_2$—$COOCH_2$—$CH=CH_2$, $CH_2$—$COOCH(CH_3)$—$COOCH_2$—$CH=CH_2$, $CH(CH_3)$—$COOCH(CH_3)$—$COOCH_2$—$CH=CH_2$ or $CH(CH_3)$—$COOCH(CH_3)$—$COOCH_2$—$CH=CH_2$;

($C_3$–$C_8$-alkenyloxy)carbonyl-$C_1$–$C_6$-alkyl: $C_1$–$C_6$-alkyl which carries a ($C_3$–$C_6$-alkenyloxy)carbonyl radical—as mentioned above—or, for example, n-hept-2-en-1-yl-O—CO, n-hept-3-en-1-yl-O—CO, n-oct-2-en-1-yl-O—CO or n-oct-3-en-1-yl-O—CO, ie. for example allyloxycarbonylmethyl, 2-(allyloxycarbonyl)ethyl or but-1-en-4-yloxycarbonylmethyl;

$C_3$–$C_8$-alkynyl: for example propargyl, n-but-1-yn-3-yl, n-but-1-yn-4-yl, n-but-2-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl, in particular propargyl;

$C_2$–$C_8$-haloalkynyl: ethynyl or $C_3$–$C_6$-alkynyl as mentioned above which is partially or fully substituted by fluorine, chlorine, bromine and/or iodine, ie. for example 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

cyano-$C_3$–$C_8$-alkynyl: for example 1-cyanopropargyl, 3-cyanopropargyl, 4-cyanobut-2-yn-1-yl, 5-cyanopent-3-yn-1-yl or 6-cyanohex-4-yn-1-yl;

$C_2$–$C_4$-alkynyloxy-$C_1$–$C_4$-alkyl: $C_1$–$C_4$-alkyl which is substituted by $C_2$–$C_4$-alkynyloxy such as ethynyloxy, propargyloxy, n-but-1-yn-3-yloxy, n-but-1-yn-4-yloxy and n-but-2-yn-1-yloxy, ie. for example $CH_2$—$OC\equiv CH$, $CH_2$—$OCH_2$—$C\equiv CH$ or 2-(propargyloxy) ethyl;

($C_3$–$C_6$-alkynyloxy)carbonyl-($C_1$–$C_4$-alkoxy)carbonyl-$C_1$–$C_4$-alkyl: ($C_1$–$C_4$-alkoxy)carbonyl-$C_1$–$C_4$-alkyl as mentioned above which carries a ($C_3$–$C_6$-alkynyloxy) carbonyl group such as propargyl-O—CO, prop-2-yn-1-yl-O—CO, n-but-1-yn-1-yl-O—CO, n-but-1-yn-3-yl-O—CO, n-but-1-yn-4-yl-O—CO, n-but-2-yn-1-

O—CO, n-pent-1-yn-1-yl-O—CO, n-pent-1-yn-3-yl-O—CO, n-pent-1-yn-4-yl-O—CO, n-pent-1-yn-5-yl-O—CO, n-pent-2-yn-1-yl-O—CO, n-pent-2-yn-4-yl-O—CO, n-pent-2-yn-5-yl-O—CO, 3-methyl-but-1-yn-3-yl-O—CO, 3-methylbut-1-yn-4-yl-O—CO, n-hex-1-yn-1-yl-O—CO, n-hex-1-yn-3-yl-O—CO, n-hex-1-yn-4-yl-O—CO, n-hex-1-yn-5-yl-O—CO, n-hex-1-yn-6-yl-O—CO, n-hex-2-yn-1-yl-O—CO, n-hex-2-yn-4-yl-O—CO, n-hex-2-yn-5-yl-O—CO, n-hex-2-yn-6-yl-O—CO, n-hex-3-yn-1-yl-O—CO, n-hex-3-yn-2-yl-O—CO, 3-methylpent-1-yn-1-yl-O—CO, 3-methylpent-1-yn-3-yl-O—CO, 3-methylpent-1-yn-4-yl-O—CO, 3-methylpent-1-yn-5-yl-O—CO, 4-methylpent-1-yn-1-yl-O—CO, 4-methylpent-2-yn-4-yl-O—CO and 4-methylpent-2-yn-5-yl-O—CO, ie. for example $CH_2$—$COOCH_2$—$COOCH_2$—$CH=CH$, $CH_2$—$COOCH(CH_3)$—$COOCH_2$—$C\equiv CH$, $CH(CH_3)$—$COOCH_2$—$COOCH_2$—$C\equiv CH$ or $CH(CH_3)$—$COOCH(CH_3)$—$COOCH_2$—$C\equiv CH$;

($C_3$–$C_8$-alkynyloxy)carbonyl-$C_1$–$C_6$-alkyl: $C_1$–$C_6$-alkyl which preferably carries a ($C_3$–$C_6$-alkynyloxy) carbonyl radical as mentioned above, in particular CO—$OCH_2$—$C\equiv CH$, but-1-yn-3-yl-O—CO, but-1-yn-4-yl-O—CO or but-2-yn-1-yl-O—CO, $C_3$–$C_8$-cycloalkyl: cyclopropyl, cyclobutyl, cyclopentyl, cyclohexyl, cycloheptyl or cyclooctyl, in particular cyclopentyl or cyclohexyl;

($C_3$–$C_7$-cycloalkyloxy)carbonyl-$C_1$–$C_4$-alkyl: for example cyclopropyloxycarbonylmethyl, cyclobutyloxycarbonylmethyl, cyclopentyloxycarbonylmethyl, cyclohexyloxycarbonylmethyl, cycloheptyloxycarbonylmethyl, 1-(cyclopropyloxycarbonyl)ethyl, 1-(cyclobutyloxycarbonyl)ethyl, 1-(cyclopentyloxycarbonyl)ethyl, 1-(cyclohexyloxycarbonyl)ethyl, 1-(cycloheptyloxycarbonyl)ethyl, 2-(cyclopropyloxycarbonyl)ethyl, 2-(cyclobutylohexycarbonyl)ethyl, 2-(cyclopentyloxycarbonyl)ethyl, 2-(cyclohexyloxycarbonyl)ethyl, 2-(cycloheptyloxycarbonyl)ethyl, 3-(cyclopropyloxycarbonyl)propyl, 3-(cyclobutyloxycarbonyl)propyl, 3-(cyclopentyloxycarbonyl)propyl, 3-(cyclohexyloxycarbonyl)propyl, 3-(cycloheptyloxycarbonyl)propyl, 4-(cyclopropyloxycarbonyl)butyl, 4-(cyclobutyloxycarbonyl)butyl, 4-(cyclopentyloxycarbonyl)butyl, 4-(cyclohexyloxycarbonyl)butyl or 4-(cycloheptyloxycarbonyl)butyl, in particular cyclopentyloxycarbonylmethyl, cyclohexyloxycarbonylmethyl or 2-(cyclopentyloxycarbonyl)ethyl;

($C_3$–$C_8$-cycloalkyloxy)carbonyl-$C_1$–$C_6$-alkyl: for example cyclopropyloxycarbonylmethyl, cyclobutyloxycarbonylmethyl, cyclopentyloxycarbonylmethyl, cyclohexyloxycarbonylmethyl, cycloheptyloxycarbonylmethyl, cyclooctyloxycarbonylmethyl, 1-(cyclopropyloxycarbonyl)ethyl, 1-(cyclobutyloxycarbonyl)ethyl, 1-(cyclopentyloxycarbonyl)ethyl, 1-(cyclohexyloxycarbonyl)-ethyl, 1-(cycloheptyloxycarbonyl)ethyl, 1-(cyclooctyloxycarbonyl)ethyl, 2-(cyclopropyloxycarbonyl)ethyl, 2-(cyclobutyloxycarbonyl)ethyl, 2-(cyclopentyloxycarbonyl)ethyl, 2-(cyclohexyloxycarbonyl)ethyl, 2-(cycloheptyloxycarbonyl)ethyl, 2-(cyclooctyloxycarbonyl)ethyl, 3-(cyclopropyloxycarbonyl)propyl, 3-(cyclobutyloxycarbonyl)propyl, 3-(cyclopentyloxycarbonyl)propyl, 3-(cyclohexyloxycarbonyl)propyl, 3-(cycloheptyloxycarbonyl)propyl, 3-(cyclooctyloxycarbonyl)propyl, 4-(cyclopropyloxycarbonyl)butyl, 4-(cyclobutyloxycarbonyl)butyl, 4-(cyclopentyloxycarbonyl)butyl, 4-(cyclohexyloxycarbonyl)butyl, 4-(cycloheptyloxycarbonyl)butyl, 4-(cyclooctyloxycarbonyl)butyl, 5-(cyclopropyloxycarbonyl)pentyl, 5-(cyclobutyloxycarbonyl)pentyl, 5-(cyclopentyloxycarbonyl)pentyl, 5-(cyclohexyloxycarbonyl)pentyl, 5-(cycloheptyloxycarbonyl)pentyl, 5-(cyclooctyloxycarbonyl)pentyl, 6-(cyclopropyloxycarbonyl)hexyl, 6-(cyclobutyloxycarbonyl)hexyl, 6-(cyclopentyloxycarbonyl)hexyl, 6-(cyclohexyloxycarbonyl)hexyl, 6-(cycloheptyloxycarbonyl)hexyl or 6-(cyclooctyloxycarbonyl)hexyl, in particular cyclopentyloxycarbonylmethyl, cyclohexyloxycarbonylmethyl or 2-(cyclopentyloxycarbonyl)ethyl;

$C_5$–$C_8$-cycloalkenyl: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept3-enyl, cyclohept-4-enyl, cyclooct-1-enyl, cyclooct-2-enyl, cyclooct-3-enyl or cyclooct-4-enyl, in particular cyclopent-1-enyl, cyclopent-2-enyl, cyclohex-1-enyl or cyclohex-2-enyl;

($C_1$–$C_4$-alkoxy)carbonyl-$C_3$–$C_7$-cycloalkyl: for example methoxycarbonylcyclopentyl, ethoxycarbonylcyclopentyl, methoxycarbonylcyclohexyl or ethoxycarbonylcyclohexyl.

Preferred with a view to the use of the substituted 2-benz (o)ylpyridines I as herbicides and/or compounds having dessicant/defoliant action are those compounds where the variables have the following meanings, in each case either on their own or in combination:

is zero;

X is carbonyl or methylene, in particular methylene;

$R^1$ is $C_1$–$C_4$-haloalkyl, in particular trifluoromethyl;

$R^2$ is halogen, in particular chlorine;

$R^3$ is halogen, in particular chlorine;

$R^4$ is halogen, in particular chlorine;

$R^5$ is —$OR^8$, —CO—$OR^8$, —CO—N($R^9$,$R^{10}$) or —CH=N—$OR^{13}$, in particular —$OR^8$;

$R^6$ is hydrogen or halogen, in particular hydrogen;

$R^7$ is hydrogen or halogen, in particular hydrogen;

$R^8$ is hydrogen, $C_1$–$C_8$-alkyl, $C_3$–$C_8$-alkenyl, $C_3$–$C_8$-alkynyl, hydroxycarbonyl-$C_1$–$C_4$-alkyl, ($C_1$–$C_8$-alkoxy)carbonyl-$C_1$–$C_6$-alkyl, ($C_3$–$C_8$-alkenyloxy) carbonyl-$C_1$–$C_6$-alkyl, ($C_3$–$C_8$-alkynyloxy)carbonyl-$C_1$–$C_6$-alkyl, $C_1$–$C_4$-alkoxy-($C_1$–$C_4$-alkoxy)carbonyl- $C_1$–$C_4$-alkyl, ($C_1$–$C_4$-alkoxy)carbonyl-($C_1$–$C_4$-alkoxy) carbonyl-$C_1$–$C_4$-alkyl,

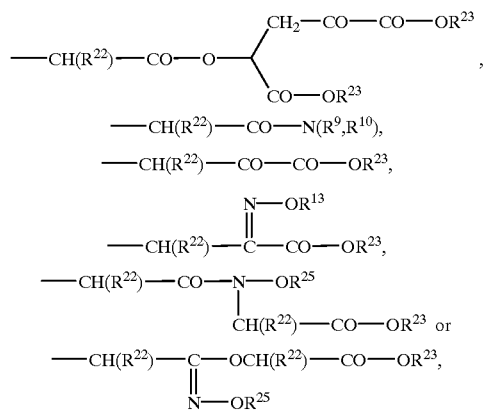

in particular hydrogen, $C_1$–$C_8$-alkyl, $C_3$–$C_8$-alkenyl, $C_3$–$C_8$-alkynyl, ($C_1$–$C_8$-alkoxy)carbonyl-$C_1$–$C_6$-alkyl, —CH($R^{22}$)—CO—N($R^9$,$R^{10}$), —CH($R^{22}$)—CO—CO—$OR^{23}$ or

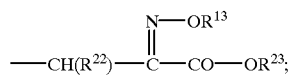

$R^9$ and $R^{10}$ are each hydrogen, $C_1$–$C_8$-alkyl or ($C_1$–$C_4$-alkoxy)carbonyl-$C_1$–$C_4$-alkyl, in particular $C_1$–$C_8$-alkyl;

$R^{13}$ is hydrogen, $C_1$–$C_8$-alkyl, $C_3$–$C_8$-alkenyl, $C_3$–$C_8$-alkynyl or ($C_1$–$C_4$-alkoxy)carbonyl-$C_1$–$C_4$-alkyl, in particular $C_1$–$C_8$-alkyl;

$R^{22}$ is hydrogen, $C_1$–$C_8$-alkyl, $C_3$–$C_8$-alkenyl or $C_3$–$C_8$-alkynyl, in particular $C_1$–$C_8$-alkyl;

$R^{23}$ is hydrogen, $C_1$–$C_8$-alkyl, $C_3$–$C_8$-alkenyl or $C_3$–$C_8$-alkynyl, in particular $C_1$–$C_8$-alkyl;

$R^{25}$ is hydrogen, $C_1$–$C_8$-alkyl, $C_3$–$C_8$-alkenyl or $C_3$–$C_8$-alkynyl, in particular $C_1$–$C_8$-alkyl.

The substituted 2-benz(o)ylpyridines of the formula I can be obtained in a variety of ways, for example by one of the following processes:

Process A

Reaction of substituted pyridines of the formula II with benzylnitriles of the formula III in the presence of a base {cf. for example R. J. Wolters et al., J. Pharmaceut. Sciences 64, (1975) 2013; Z.-T. Huang et al., Synth. Commun. 23, (1993), 591; H. Yamanaka and S. Ohba, Heterocycles 3, (1990), 895}:

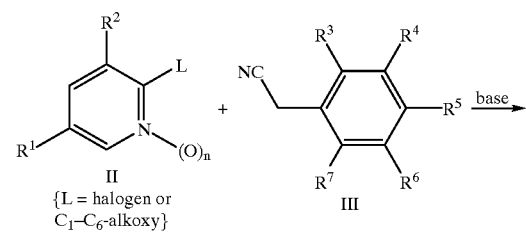

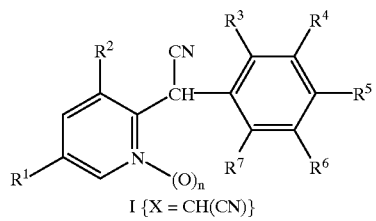

In general, the reaction is carried out in an inert solvent or diluent, in particular in a dipolar aprotic solvent, for example in N,N-dimethylformamide, N-methylpyrrolidone or in an ether such as diethyl ether, 1,2-diethoxyethane, tetrahydrofuran and dioxane.

Suitable bases are, for example, the alkali metal hydrides, amides, carbonates and bicarbonates, and furthermore nitrogen bases such as triethylamine, pyridine and 4-dimethylaminopyridine. Additionally, it is possible to employ the alkali metal salts of bulky alcohols such as potassium tert-butoxide.

The reaction temperature is generally from 0 to 150° C.

In general, the reactants are employed in approximately stochiometrical amounts, but it may be advantageous to use an excess of one of the components, for example to obtain as complete a conversion of the other component as possible.

The substituted pyridines II and benzylnitriles III are either known, some of them even being commercially available, or they are easily prepared by conventional methods. For the preparation of benzylnitriles from benzyl halides see, for example, V. G. Telang and C. J. Smith, J. Pharm. Sci. 59, (1970), 1521.

Process B

Partial hydrolysis of compounds I where X=CH(CN), for example in conc. sulfuric acid {cf. for example R. J. Wolters et al., J. Pharm. Sci. 64, (1975), 2013}, leads to substituted 2-benz(o)ylpyridines I where X=CH—$CONH_2$, the alcoholysis of which {again, cf. for example R. J. Wolters et al.} affords 2-benz(o)ylpyridines I where X=CH—CO—O ($C_1$–$C_4$-alkyl):

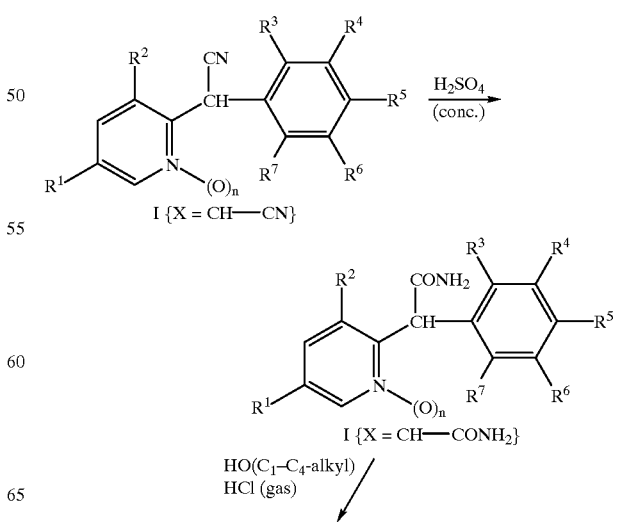

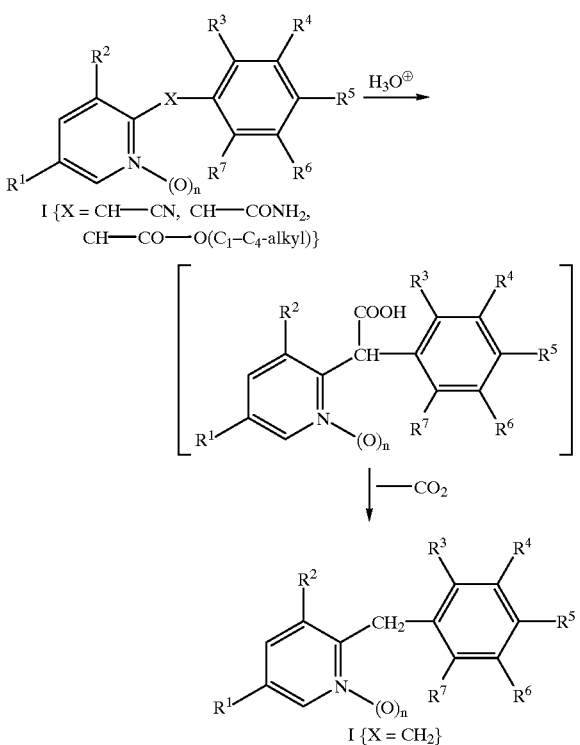

The hydrolysis with conc. sulfuric acid is usually carried out at from 0 to 50° C., preferably at room temperature.

The subsequent alcoholysis is preferably carried out in excess alcohol HO(C$_1$–C$_4$-alkyl) as solvent, but it is also possible to use other inert solvents/diluents. The alcoholysis is catalyzed by mineral acids such as hydrogen chloride.

The reaction is usually carried out at from 0 to 150° C., preferably at the boiling point of the alcohol HO(C$_1$–C$_4$-alkyl).

Process C

Hydrolysis of 2-benz(o)ylpyridines of the formula I where X is CH—CN, CH—CONH$_2$ or CH—CO—O(C$_1$–C$_4$-alkyl) in the presence of an aqueous acid:

Suitable acids are for example mineral acids such as hydrochloric acid, hydrobromic acid and sulfuric acid or organic acids such as trifluoroacetic acid.

The preferred solvent is water which, if desired, may be mixed with an inert cosolvent, for example acetic acid or dimethyl sulfoxide, in order to increase the solubility of the reactants.

The reaction is usually carried out at from 0 to 150° C., preferably at the boiling point of the solvent.

It is usually not possible to isolate the carboxylic acids which are formed as intermediates; in most instances, they spontaneously decarboxylate under the stated reaction conditions.

Process D

Oxidation of 2-benz(o)ylpyridines of the formula I {X=CH—CN} with oxygen (air) in the presence of a base {cf. for example M. S. Kharasch and G. Sosnovsky, Tetrahedron 3, (1958), 97; H. G. Aurich, Tetrahedron Lett. 12, (1964), 657; S. S. Kulp, Org. Prep. and Proced. 2, (1970), 137; A. Donetti et al., Synthesis 1980, 1009; J. F. Wolfe et al., J. Het. Chem. 24, (1987), 1061; H. Yamanaka and S. Ohba, Heterocycles 31, (1990), 895}:

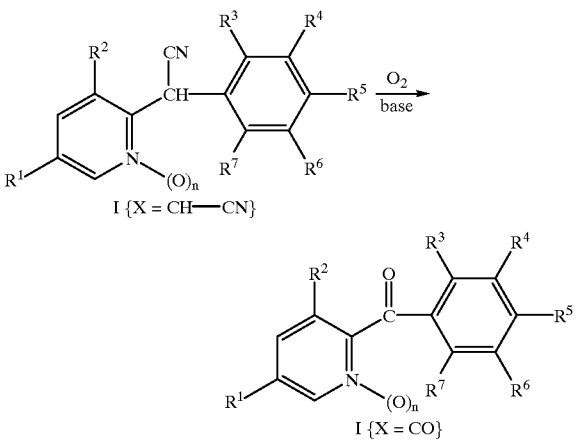

Suitable bases are, for example, the alkali metal hydrides, amides, carbonates and bicarbonates, and furthermore nitrogen bases such as triethylamine, pyridine and 4-dimethylaminopyridine. Additionally, it is possible to employ the alkali metal salts of bulky alcohols such as potassium tert-butoxie.

Suitable solvents are both protic solvents, for example alcohols such as methanol and ethanol, and dipolar aprotic solvents, for example dimethylsulfoxide or ether such as tetrahydrofuran and dioxane.

The reaction is usually carried out at temperatures from 0 to 50° C., preferably at room temperature. If desired, the progress of the reaction can be accelerated by using a phase transfer catalyst such as triethylbenzylammonium chloride.

Process E

Reduction of 2-benz(o)ylpyridines I {X=CO} with complex hydrides such as NaBH$_4$ and LiAlH$_4$ or by catalytic hydrogenation in the presence of a transition metal catalyst, for example Raney nickel or platinum/carbon, in a conventional manner {cf. for example C. Vaccher et al., J. Het. Chem. 26, (1989), 811–815; G. R. Newkome et al., J. Org. Chem. 49, (1984), 2961–2971; A. Garcia et al., Tetrahedron Lett. 34, (1993), 1797–1798; M. Takeshita et al., Heterocycles 35, (1993), 879–884; M. Takemoto et al., Chem. Pharm. Bull. 42, (1994), 802–805}:

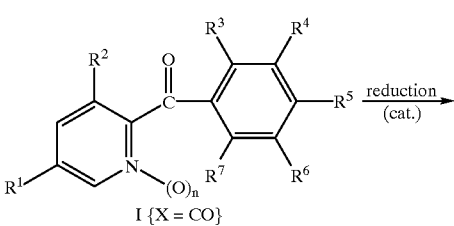

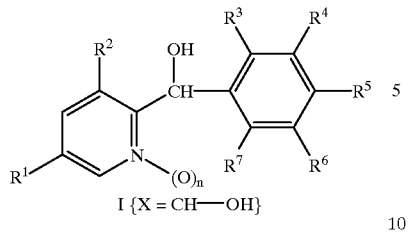

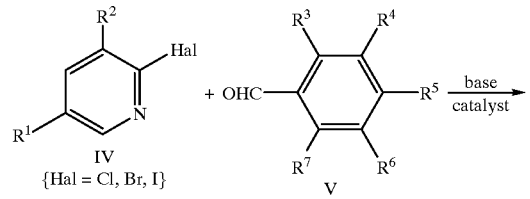

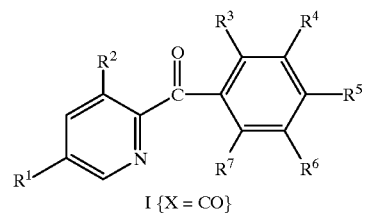

The products I where X=CH—OH can subsequently be alkylated in the presence of a base using alkyl halides X-(C$_1$–C$_4$-alkyl), X being chlorine, bromine or iodine {cf. for example D. E. Beattie et al., J. Med. Chem. 20, (1977), 714–718; J. Crosby et al., Tetrahedron Lett. 30, (1989), 3849–3852; S. jriuchijima et al., J. Am. Chem. Soc. 96, (1974), 4280; S. Sakuraba et al., Tetrahedron: Asymmetry 4, (1993), 1457–1460; Ya. G. BaL'on et al., Ukr. Khim. Zh. (Russ. Ed.) 57, (1991), 191–195}:

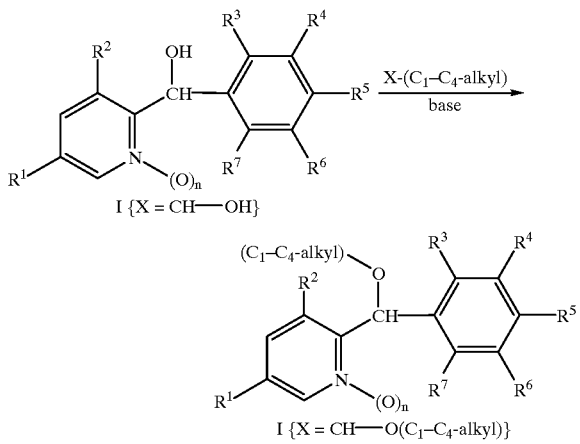

Suitable bases are, for example, alkali metal hydroxides such as sodium hydroxide, alkali metal hydrides such as sodium hydride, alkali metal amides such as sodium amide or alkali metal salts of alcohols, such as potassium tert-butoxide.

The reaction is usually carried out in an inert solvent/diluent, both dipolar aprotic solvents, for example N,N-dimethylformamide, dimethylsulfoxide or ethers such as diethyl ether, tetrahydrofuran and 1,4-dioxane, and protic solvents, for example alcohols such as tert-butanol, being suitable solvents.

The reaction is usually carried out at a temperature from 0 to 150° C., preferably at 20 to 1000° C.

Process E

Nucleophilic benzoylation of halopyridines of the formula IV with benzaldehydes V in the presence of a base and a catalyst {cf. for example H. Stetter, Angew. Chem. 88, (1976), 695; A. Miyashita et al., Chem. Pharm. bull. 38, (1990), 1147–1152; A. Miyashita et al., ibid 40, (1992), 43–48 and 2627–2631; A. Miyashita et al., ibid 42, (1994), 2017–2022}:

Suitable bases are, for example, alkali metal hydrides such as sodium hydride or alkali metal amides such as sodium amide.

Suitable solvents are, for example, dipolar aprotic solvents, for example N,N-dimethylformamide, dimethylsulfoxide or cyclic ethers such as tetrahydrofuran and 1,4-dioxane.

Suitable catalysts are in particular (substituted) (benz) imidazolium salts and (substituted) (benzo)thiazolium salts, for example 1,3-dimethylimidazolium chloride, 1,3-dimethylimidazolium bromide, 1,3-dimethylimidazolium iodide, 1,3-benzimidazolium chloride, 1,3-benzimidazolium bromide and 1,3-dimethylbenzimidazolium iodide.

The amount of catalyst is up to 50%, preferably from 5 to 20%, based on the molar amount of the halopyridine used.

The reaction is usually carried out at temperatures from 0 to 150° C., preferably at temperatures from 20 to 100° C.

Process G

Reaction of halopyridines IV with benzylmagnesium halides VI or benzylzinc halides VII, if appropriate in the presence of a transition metal catalyst {cf. for example E. Negishi et al., J. org. Chem. 42, (1977), 1821 and M. Kumada et al., Tetrahedron Lett. 21, (1980), 845}:

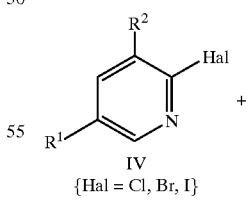

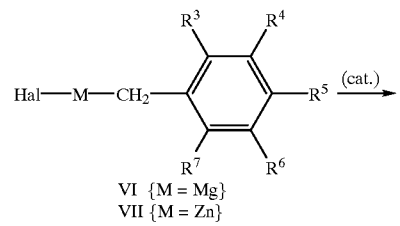

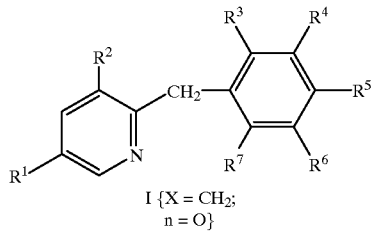

I {X = CH₂; n = 0}

The compounds VI and VII are easily prepared from the corresponding benzyl halides and magnesium or zinc, for example according to M. Gaudemar, Bull. Soc. Chim. Fr., 1962, p. 974.

Suitabale catalysts are in particular nickel catalysts, for example Ni[P(phenyl)₃]₄ or Ni[P(phenyl)₃]₂Cl₂, and palladium catalysts, for example Pd[P(phenyl)₃]₄, Pd[P(phenyl)₃]₂Cl₂, Pd[1,2-bis(diphenylphosphino)ethane]Cl₂, Pd[1,4-bis(diphenylphosphino)butane]Cl₂ or Pd[1,2'-bis(diphenylphosphino)ferrocene]Cl₂.

The reaction is usually carried out in an inert organic solvent, for example in an ether such as diethyl ether and tetrahydrofuran.

The reaction is usually carried out at from 0 to 150° C., preferably from 20 to 100° C.

Process H

Oxidation of substituted 2-benz(o)ylpyridines of the formula I where n is zero in a conventional manner {cf. for example A. Albini and S. Pietra, Heterocyclic N-Oxides, CRC-Press Inc., Boca Raton, USA 1991; H. S. Mosher et al., Org. Synth. Coll. Vol. IV, 1963, p. 828; E. C. Taylor et al., Org. Synth. Coll. Vol. IV, 1963, p. 704; T. W. Bell et al., Org. Synth. 69, (1990), 226}:

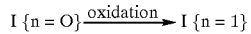

I {n = O} —oxidation→ I {n = 1}

The oxidizing agents conventionally used for oxidizing the pyridine ring include, for example, peracetic acid, trifluoroperacetic acid, perbenzoic acid, m-chloroperbenzoic acid, monopermaleic acid, magnesium monoperphthalate, sodium perborate, Oxonee (contains peroxidisulfate), pertungstic acid and hydrogen peroxide.

Suitable solvents are, for example, water, sulfuric acid, carboxylic acids such as acetic acid and trifluoroacetic acid and halogenated hydrocarbons such as dichloromethane and chloroform.

The oxidation usually succeeds at temperatures from 0° C. to the boiling point of the reaction mixture.

The oxidizing agent is usually employed in at least equimolar amounts, based on the starting material. In specific instances, a large excess of oxidizing agent may be advantageous.

Unless stated otherwise, all the processes described above are advantageously carried out at atmospheric pressure or under the autogenous pressure of the reaction mixture in question.

The work-up of the reaction mixtures is usually carried out in a conventional manner. Unless stated otherwise in the processes described above, the products of value are obtained, for example, after the dilution of the reaction solution with water by filtration, crystallization or solvent extraction, or by removing the solvent, partitioning the residue in a mixture of water and a suitable organic solvent and work-up of the organic phase to afford the product.

The substituted 2-benz(o)ylpyridines I can be obtained as isomer mixtures in the preparation; however, if desired, these can be separated into largely pure isomers using customary methods such as crystallization or chromatography, including chromatography over an optically active adsorbent. Pure optically active isomers can be prepared advantageously from suitable optically active starting materials.

Agriculturally useful salts of the compounds I can be formed by reaction with a base of the corresponding cation, preferably an alkali metal hydroxide or hydride, or by reaction with an acid of the corresponding anion, preferably of hydrochloric acid, hydrobromic acid, sulfuric acid, phosphoric acid or nitric acid.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, for use as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Taking into account the diversity of application methods, the compounds I, or herbicidal compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa , Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

In addition, the compounds I may also be used in crops which tolerate the action of herbicides owing to breeding, including genetic engineering methods.

Moreover, the substituted 2-benz(o)ylpyridines I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which is made possible by dehiscence, or reduction of the adherence to the tree, both concentrated over a period of time, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee a very fine distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substituted 2-benz(o)ylpyridines I, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound I. The active compounds are employed in a purity of from 90% to 100%, preferably 95% to 100% (according to the NMR spectrum).

The formulation examples which follow illustrate the preparation of such products:

I. 20 parts by weight of the compound No. 2 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 108 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 118 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 460 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 369 are mixed with 97 parts by weight of finely divided kaolin. This gives a dust which comprises 3% by weight of active compound.

VI. 20 parts by weight of the active compound No. 470 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil.This gives a stable oily dispersion.

VII. 1 part by weight of the compound No. 490 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active compound. This gives a stable emulsion concentrate.

VIII. 1 part by weight of the compound No. 491 is dissolved in a mixture composed of 80 parts by weight of cyclohexane and 20 parts by weight of Wettol® EM 31 (=nonionic emulsifier based on ethoxylated castor oil; BASF AG). The mixture can then be diluted with water to the desired concentration of active compound. This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 2-benz(o)ylpyridines I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, Lmidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1

3-Chloro-2-[1-(4-chlorophenyl)-1-cyanomethyl]-5-trifluoromethylpyridine (Process A)

1.65 g of sodium hydride (80% suspension in mineral oil) were washed with 30 ml of anhydrous N,N-dimethylformamide to remove the mineral oil. The resulting sodium hydride was admixed with 25 ml of N,N-dimethylformamide and a solution of 7.6 g of 4-chlorobenzyl cyanide in 25 ml of N,N-dimethylformamide was added dropwise within 20 minutes. With evolution of gas, a red suspension was formed which was stirred for a further 15 minutes. Subsequently, 10.8 g of 2,3-dichloro-5-trifluoromethylpyridine were added dropwise to the reaction mixture within 20 minutes in an exothermic reaction. After the addition, the reaction mixture was stirred for another 20 minutes and then stirred into 2 l of water. The product was extracted from the aqueous phase with tert-butyl methyl-ether (three times 200 ml). The combined organic phases were finally dried over magnesium sulfate and then concentrated. The crude product was purified by silica gel chromatography (eluent: cyclohexane/ethyl acetate =4:1). Yield: 6.9 g (42%) of a colorless oil; $^1$H NMR (270 MHz; in CDCl$_3$): δ[ppm]=5.78 (s,1H), 7.36 (d,2H), 7.45 (d,2H), 7.98 (s,1H), 8.84 (s,1H).

Example 2

3-Chloro-2-[1-(2,3-dichlorophenyl)-1-cyanomethyl]-5-trifluoromethylpyridine (Process A)

By the method of Example 1, 10.0 g of a colorless oil were obtained from 1.65 g of sodium hydride suspension, 9.3 g of 2,3-dichlorobenzyl cyanide and 10.8 g of 2,3-dichloro-5-trifluoromethylpyridine. Yield: 55%; $^1$H NMR (400 MHz; in CDCl$_3$): δ[ppm]=6.20 (s,1H), 7.30 (t,1H), 7.50–7.56 (m,2H), 8.03 (s,1H), 8.78 (s,1H).

Example 3

2-[1Carbamoyl-1-(4-chlorophenyl)methyl]-3-chloro-5-trifluoromethylpyridine (Process B)

At 23° C., 6.0 g of 3-chloro-2-[1-(4-chlorophenyl)-1-cyanomethyl]-5-trifluoromethylpyridine (prepared by the method of Example 1) were stirred in 30 ml of 96% strength sulfuric acid for 16 hours. The reaction mixture was then carefully stirred into 200 ml of ice water during which the product crystallized out. The solid was separated off, washed successively with water and n-hexane and dried. Yield: 5.5 g (87%) of colorless crystals; mp.: 135–136° C.

Example 4

3-Chloro-2-[1-(4-chlorophenyl)-1-methoxycarbonyl-methyl]-5-trifluoromethylpyridine (Process B)

Hydrogen chloride gas was introduced into a solution of 3.0 g of 2-[1-carbamoyl-1-(4-chlorophenyl)methyl]-3-chloro-5-trifluoromethylpyridine (prepared by the method of Example 3) in 100 ml of anhydrous methanol for 5 hours. The mixture was subsequently stirred for another 16 hours and excess hydrogen chloride was removed by passing nitrogen through the mixture. The methanol was separated off and the crude product was purified by silica gel chromatography (eluent: cyclohexane/tert-butyl methyl ether 50:1). Yield: 1.3 g (42%) of colorless crystals; mp.: 103–104° C.

Example 5

3-Chloro-2-(4-chlorobenzyl)-5-trifluoromethylpyridine (Process C)

4.3 g of 3-chloro-2-[1-(4-chlorophenyl)-1-cyanomethyl]-5-trifluoromethylpyridine (prepared by the method of Example 1) were heated under reflux in 50 ml of 47% strength aqueous hydrogen bromide solution for 3 hours and then stirred for another 68 hours at 23° C. The reaction mixture was subsequently poured into 500 ml of ice water. The mixture was stirred for a further 30 minutes and the solid that had formed was separated off, washed with water and then dried. Yield: 3.0 g (75%) of colorless crystals; mp.: 54–56° C.).

Example 6

3-Chloro-2-(2,3-dichlorobenzyl)-5-trifluoromethylpyridine (Process C)

By the method of Example 5, 6.3 g of a colorless oil were obtained from 7.9 g of 3-chloro-2-[1-(2,3-dichlorophenyl)-1-cyanomethyl]-5-trifluoromethylpyridine (prepared by the method of Example 2). Yield: 86%; $^1$H NMR (270 MHz; in CDCl$_3$): δ[ppm]=4.50 (s,2H), 7.02 (d,1H), 7.15 (t,1H), 7.40 (d,1H), 7.93 (s,1H), 8.67 (s,1H).

Example 7

3-Chloro-2-(4-chlorobenzoyl)-5-trifluoromethylpyridine 3.0 g of sodium hydride (80% suspension in mineral oil) were washed with anhydrous dioxane to remove the mineral oil. The resulting sodium hydride was admixed first with 100 ml of dioxane and then, under a nitrogen atmosphere, successively with 21.6 g of 2,3-dichloro-5-trifluoromethylpyridine, 14.1 g of p-chlorobenzaldehyde and 2.24 g of 1,3-dimethylimidazolium iodide. This reaction mixture was stirred at 50° C. for 1 hour and at 23° C. for 65 hours. For work-up, the mixture was diluted with 200 ml of water and then concentrated to half its volume. The product was subsequently extracted with methylene chloride (three times 50 ml). The combined organic phases were washed with 50 ml of water, dried over sodium sulfate and then concentrated. The crude product was purified by vacuum distillation. Yield: 22.4 g (70%) of a yellow liquid; Boiling range: 126–139° C./0.65 mbar; purity: 95%; $^1$H NMR (270 MHz; in CDCl$_3$): δ[ppm]=7.48 (d,2H), 7.79 (d,2H), 8.12 (s,1H), 8.83 (s,1H).

Example 8

3-Chloro-2-(4-chlorobenzoyl)-5-trifluoromethylpyridine (Process D)

A solution of 2.0 g of 3-chloro-2-[1-(4-chlorophenyl)-1-cyanomethyl]-5-trifluoromethylpyridine (prepared by the method of Example 1) in 20 ml of dimethyl sulfoxide was admixed with a solution of 2.0 g of potassium carbonate in 3 ml of water, and the mixture was then stirred at 23° C. for 3 days under air. For work-up, the reaction mixture was poured into 200 ml of water. The product of value was then extracted with tert-butyl methyl ether (three times 80 ml). The combined organic phases were washed with water (two times 50 ml each), dried over sodium sulfate and finally concentrated. The resulting black oil was purified by Kugelrohr distillation under reduced pressure. Yield: 1.2 g (62%) of a light-yellow oil; boiling range: 110–120° C. (0.3 mbar); $^1$H NMR see Ex. 7.

Example 9

3-Chloro-2-(4-chlorobenzoyl)-5-trifluoromethylpyridine (Process A+D)

16.5 g of sodium hydride (80% suspension in mineral oil) were washed with anhydrous N,N-dimethylformamide to remove the mineral oil. The sodium hydride was then admixed with 100 ml of N,N-dimethylformamide and a solution of 37.9 g of 4-chlorobenzyl cyanide in 100 ml of N,N-dimethylformamide was then added dropwise (exotherm). After the addition, the mixture was stirred for another 15 minutes. 54.0 g of 2,3-dichloro-5-trifluoromethylpyridine were then added dropwise to the reaction mixture which heated up considerably in the process and was kept at about 50° C. by external cooling. After the addition, the mixture was stirred for another 20 hours at 23° C. Air which had been dried over blue gel was then passed through the mixture for 4 days. For work-up, the reaction mixture was poured into 600 ml of ice-water. The product of value was then extracted with tert-butyl methyl ether (three times 200 ml). The combined organic phases were washed with water (two times 100 ml each), dried over sodium sulfate and finally concentrated. The crude product was purified by silica gel chromatography (eluent: cyclohexane/tert-butyl methyl ether 9:1). Yield: 50.1 g (62%) of a light-yellow oil; purity (GC); 94.6%; $^1$H NMR see Ex. 7.

Example 10

3-Chloro-2-[1-(4-chlorophenyl)-1-hydroxymethyl]-5-trifluoromethylpyridine (Process E)

With ice-cooling, 0.36 g of sodium borohydride were added a little at a time to a solution of 6.0 g of 3-chloro-2-(4-chlorobenzoyl)-5-trifluoromethylpyridine in 10 ml of anhydrous ethanol. The reaction mixture was stirred at 23° C. for 20 hours, after which 50 ml of 10% strength hydrochloric acid were carefully added dropwise. The ethanol was evaporated and the product was subsequently extracted with tert-butyl methyl ether (three times 30 ml). The combined organic phases were dried over sodium sulfate and then concentrated. The crude product was purified by silica gel chromatography (eluent: cyclohexane/tert-butyl methyl ether=9:1). Yield: 3.6 g (60%) of a colorless oil; $^1$H NMR (270 MHz; in CDCl$_3$): δ[ppm]=5.02 (d,1H), 6.02 (d,1H), 7.33–7.41 (m,4H), 7.91 (s,1H), 8.81 (s,1H).

Example 11

3-Chloro-2-[1-(4-chlorophenyl)-1-methoxymethyl]-5-trifluoromethylpyridine (Process E)

0.2 g of sodium hydride (80% suspension in mineral oil) were washed with anhydrous N,N-dimethylformamide to remove the mineral oil. The sodium hydride was initially admixed with 50 ml of N,N-dimethylformamide and a solution of 2.1 g of 3-chloro-2-[1-(4-chlorophenyl)-1-hydroxymethyl]-5-trifluoromethylpyridine in 10 ml of N,N-dimethylformamide was then added dropwise. The mixture was subsequently stirred for another 15 minutes. After the dropwise addition of 1.1 g of methyl iodide, the mixture was stirred at 23° C. for a further 20 hours. The reaction mixture was then poured into 200 ml of ice-water. The product was extracted from the aqueous phase using tert-butyl methyl ether (three times 70 ml). The combined organic phases were washed with water (two times 50 ml each), dried over sodium sulfate and finally concentrated. The crude product was purified by silica gel chromatography (eluent: cyclohexane/tert-butyl methyl ether 100:1). Yield: 1.1 g (50%) of a colorless oil. $^1$H NMR (270 MHz; in CDCl$_3$): δ[ppm]=3.44 (s,3H), 5.83 (s,1H), 7.33 (d,2H), 7.48 (d,2H), 7.90 (s,1H), 8.85 (s,1H).

Example 12

3-Chloro-2-(4-chlorobenzoyl)-5-trifluoromethylpyridine (Process F)

With stirring, 21.6 g of 2,3-dichloro-5-trifluoromethylpyridine, 14.1 g of 4-chlorobenzaldehyde and 2.24 g of 1,3-dimethylimidazolium iodide were added in succession to a suspension of 3.0 g of sodium hydride (80% by weight suspension in mineral oil) in 100 ml of anhydrous dioxane. The mixture was then stirred (under a nitrogen atmosphere) for 11 hours at 50° C. and then for 60 hours at 22° C. The reaction mixture was diluted with 200 ml of water and most of the dioxane was distilled off under reduced pressure. The product was extracted from the residue with methylene chloride (three times 100 ml). The combined organic phases were washed with 50 ml of water, dried over sodium sulfate and finally concentrated. Distillation of the residue at 0.65 mbar (boiling range: 126–139° C.) gave 22.4 g of a colorless oil. Yield: 70% (purity: about 95%); $^1$H-NMR see Ex. 7.

Example 13

3-Chloro-2-[1-(2,3-dichloro-4-methoxyphenyl)-1-cyanomethyl]-5-trifluoromethylpyridine (Process A)

Intermediate: 2,3-Dichloro-4-methoxybenzyl bromide

At 30° C., 55.0 g of 2,3-dichloroanisole were dissolved in 155 ml of glacial acetic acid and admixed with 9.6 g of paraformaldehyde. 65 ml of a 30% strength by weight solution of HBr in glacial acetic acid were then added and the mixture was stirred at 90° C. for 5 hours. The reaction mixture was subsequently allowed to cool and then poured into 800 ml of ice-water. The crystalline crude product was separated off, washed with water and recrystallized from n-hexane. Yield: 21 g (78%) of white crystals; mp.: 101–102° C.

Intermediate: 2,3-Dichloro-4-methoxybenzyl cyanide

With stirring, a solution of 68 g of 2,3-dichloro-4-methoxybenzyl bromide in 220 ml of dimethyl sulfoxide was added dropwise to a suspension of 15 g of anhydrous sodium cyanide in 250 ml of anhydrous dimethyl sulfoxide. The mixture was subsequently heated to reflux temperature for 5 hours under an atmosphere of nitrogen. After cooling, the reaction mixture was poured into 1.5 l of ice-water and the resulting solid product was separated off, washed with water and purified by stirring with petroleum ether (at 40–60° C.). Yield: 51 g (94%) of white crystals; mp.: 118–119° C.

By the method of Example 1, 39.2 g of white crystals were obtained using 38.9 g of 2,3-dichloro-5-trifluoromethylpyridine, 38.9 g of 2,3-dichloro-4-methoxybenzylnitrile, 5.95 g of an 80% strength by weight suspension of sodium hydride in mineral oil and 220 ml of dimethylformamide. Yield: 55%; mp.: 174–176° C.

Example 14

3-Chloro-2-[2,3-dichloro-4-hydroxybenzyl)-5-trifluoromethylpyridine (Process C)

By method of Example 5, 20 g of product of value (white crystals) were obtained from 38 g of 3-chloro-2-[1-(2,3-dichloro-4-methoxyphenyl)-1-cyanomethyl]-5-trifluoromethylpyridine. Yield: 60%; mp.: 159–161° C.

Example 15

Methyl 2-[2,3-dichloro-4-([3-chloro-5-trifluoromethylpyridin-2-yl]methyl)phenoxy]acetate At 23° C., 2.0 g of 3-chloro-2-(2,3-dichloro-4-hydroxybenzyl)-5-trifluoromethylpyridine, 1.5 g of anhydrous potassium carbonate and 1.0 g of methyl bromoacetate were stirred in 60 ml of anhydrous dimethylformamide for 16 hours. The reaction mixture was then poured into 400 ml of ice-water. The resulting solid product was separated off, washed with water and purified by stirring in n-hexane. Yield: 2.4 g (100%; white crystals); mp.: 110–111° C.

The compounds described above and other substituted 2-benz(o)ylpyridines I which likewise have been or can be prepared by one of the described processes are listed in Tables 1 and 2 below:

TABLE 1

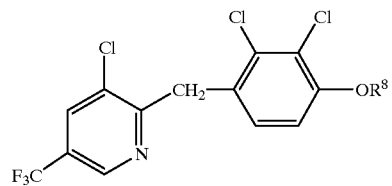

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 1 | —H | |
| 2 | —CH$_3$ | 88° C. |
| 3 | —C$_2$H$_5$ | |
| 4 | —CH$_2$—C$_2$H$_5$ | |
| 5 | —CH(CH$_3$)$_2$ | |
| 6 | —CH$_2$—CH$_2$—C$_2$H$_5$ | |
| 7 | —CH$_2$—CH(CH$_3$)$_2$ | |
| 8 | —CH(CH$_3$)—C$_2$H$_5$ | |
| 9 | —C(CH$_3$)$_3$ | |
| 10 | —CH$_2$.CH$_2$—CH$_2$—C$_2$H$_5$ | |
| 11 | cyclopropyl | |
| 12 | cyclobutyl | |
| 13 | cyclopentyl | |

TABLE 1-continued

I {n = 0; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 14 | cyclohexyl | |
| 15 | —CF$_3$ | |
| 16 | —CHF$_2$ | |
| 17 | —CH$_2$—CN | |
| 18 | —CH$_2$—CH$_2$—CN | |
| 19 | —CH$_2$—CH$_2$—CH$_2$—CN | |
| 20 | —CH$_2$—CH$_2$—CH$_2$—CH$_2$—CN | |
| 21 | —CH$_2$—OCH$_3$ | |
| 22 | —CH$_2$—OC$_2$H$_5$ | |
| 23 | —CH$_2$—OCH$_2$—C$_2$H$_5$ | |
| 24 | —CH$_2$—OCH(CH$_3$)$_2$ | |
| 25 | —CH$_2$—OCH$_2$—CH$_2$—C$_2$H$_5$ | |
| 26 | —CH$_2$—OCH(CH$_3$)—C$_2$H$_5$ | |
| 27 | —CH$_2$—OCH$_2$—CH(CH$_3$)$_2$ | |
| 28 | —CH$_2$—OC(CH$_3$)$_3$ | |
| 29 | —CH$_2$—OCH$_2$—CH$_2$—CH$_2$—C$_2$H$_5$ | |
| 30 | —CH$_2$—SCH$_3$ | |
| 31 | —CH$_2$—SC$_2$H$_5$ | |
| 32 | —CH$_2$—SCH$_2$—C$_2$H$_5$ | |
| 33 | —CH$_2$—SCH(CH$_3$)$_2$ | |
| 34 | —CH$_2$—SCH$_2$—CH$_2$—C$_2$H$_5$ | |
| 35 | —CH$_2$—SCH$_2$—CH(CH$_3$)$_2$ | |
| 36 | —CH$_2$—SCH(CH$_3$)—C$_2$H$_5$ | |
| 37 | —CH$_2$—SC(CH$_3$)$_3$ | |
| 38 | —CH$_2$—SCH$_2$—CH$_2$—CH$_2$—C$_2$H$_5$ | |
| 39 | —CH$_2$—SO—CH$_3$ | |
| 40 | —CH$_2$—SO—C$_2$H$_5$ | |
| 41 | —CH$_2$—SO—CH$_2$—C$_2$H$_5$ | |
| 42 | —CH$_2$—SO—CH(CH$_3$)$_2$ | |
| 43 | —CH$_2$—SO—CH$_2$—CH$_2$—C$_2$H$_5$ | |
| 44 | —CH$_2$—SO—CH$_2$—CH(CH$_3$)$_2$ | |
| 45 | —CH$_2$—SO—CH(CH$_3$)—C$_2$H$_5$ | |
| 46 | —CH$_2$—SO—C(CH$_3$)$_3$ | |
| 47 | —CH$_2$—SO—CH$_2$—CH$_2$—CH$_2$—C$_2$H$_5$ | |
| 48 | —CH$_2$—SO$_2$—CH$_3$ | |
| 49 | —CH$_2$—SO$_2$—C$_2$H$_5$ | |
| 50 | —CH$_2$—SO$_2$—CH$_2$—C$_2$H$_5$ | |
| 51 | —CH$_2$—SO$_2$—CH(CH$_3$)$_2$ | |
| 52 | —CH$_2$—SO$_2$—CH$_2$—CH$_2$—C$_2$H$_5$ | |
| 53 | —CH$_2$—SO$_2$—CH$_2$—CH(CH$_3$)$_2$ | |
| 54 | —CH$_2$—SO$_2$—CH(CH$_3$)—C$_2$H$_5$ | |
| 55 | —CH$_2$—SO$_2$—C(CH$_3$)$_3$ | |
| 56 | —CH$_2$—SO$_2$—CH$_2$—CH$_2$—CH$_2$—C$_2$H$_5$ | |
| 57 | —CH$_2$—CH=CH$_2$ | 88° C. |
| 58 | —CH(CH$_3$)—CH=CH$_2$ | |
| 59 | —CH$_2$—C(CH$_3$)=CH$_2$ | |
| 60 | —CH$_2$—CH=CH—CH$_3$ | |
| 61 | —CH$_2$—CH=C(CH$_3$)$_2$ | |
| 62 | —CH$_2$—CH$_2$—CH=CH$_2$ | |
| 63 | —CH$_2$—CH$_2$—CH=CH—CH$_3$ | |
| 64 | —CH$_2$—CH$_2$—C(CH$_3$)=CH$_2$ | |
| 65 | —CH$_2$—CH$_2$—C=C(CH$_3$)$_2$ | |
| 66 | cyclopent-2-en-1-yl | |
| 67 | cyclohex-2-en-1-yl | |
| 68 | —CH$_2$—CH=CHCl | |
| 69 | —CH$_2$—C(Cl)=CH$_2$ | |
| 70 | —CH$_2$—CH=CCl$_2$ | |
| 71 | —CH$_2$—C(Cl)=CHCl | |
| 72 | —CH$_2$—C(Cl)=CCl$_2$ | |
| 73 | —CH$_2$—C≡CH | 91° C. |
| 74 | —CH(CH$_3$)—C≡CH | |
| 75 | —CH$_2$—C≡C—CH$_3$ | |
| 76 | benzyl | |

TABLE 1-continued

I {n = 0; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 77 | o-chlorobenzyl | |
| 78 | m-chlorobenzyl | |
| 79 | p-chlorobenzyl | |
| 80 | o-methylbenzyl | |
| 81 | m-methylbenzyl | |
| 82 | p-methylbenzyl | |
| 83 | o-(OCH$_3$)benzyl | |
| 84 | m-(OCH$_3$)benzyl | |
| 85 | p-(OCH$_3$)benzyl | |
| 86 | o-(OCF$_3$)benzyl | |
| 87 | m-(OCF$_3$)benzyl | |
| 88 | p-(OCF$_3$)benzyl | |
| 89 | —CH$_2$—(o-C$_6$H$_4$)—OCH$_2$—CO—OCH$_3$ | |
| 90 | —CH$_2$—(m-C$_6$H$_4$)—OCH$_2$—CO—OCH$_3$ | |
| 91 | —CH$_2$—(p-C$_6$H$_4$)—OCH$_2$—CO—OCH$_3$ | |
| 92 | —CH$_2$—(o-C$_6$H$_4$)—OCH$_2$—CO—OC$_2$H$_5$ | |
| 93 | —CH$_2$—(m-C$_6$H$_4$)—OCH$_2$—CO—OC$_2$H$_5$ | |
| 94 | —CH$_2$—(p-C$_6$H$_4$)—OCH$_2$—CO—OC$_2$H$_5$ | |
| 95 | o-nitrophenyl | |
| 96 | m-nitrophenyl | |
| 97 | p-nitrophenyl | |
| 98 | o-cyanophenyl | |
| 99 | m-cyanophenyl | |
| 100 | p-cyanophenyl | |

TABLE 1-continued

I {n = O; X = CH₂; R¹ = CF₃; R², R³, R⁴ = Cl; R⁵ = OR⁸; R⁶, R⁷ = H}

| No. | —R⁸ | Mp./¹H NMR (in CDCl₃) [ppm] |
|---|---|---|
| 101 | —CH₂—(2-C₆H₄)—CO—OCH₃ | |
| 102 | —CH₂—(3-C₆H₄)—CO—OCH₃ | |
| 103 | —CH₂—(4-C₆H₄)—CO—OCH₃ | |
| 104 | —CH₂—(2-C₆H₄)—CO—OC₂H₅ | |
| 105 | —CH₂—(3-C₆H₄)—CO—OC₂H₅ | |
| 106 | —CH₂—(4-C₆H₄)—CO—OC₂H₅ | |
| 107 | —CH₂—CO—OH | |
| 108 | —CH₂—CO—OCH₃ | 111° C. |
| 109 | —CH₂—CO—OC₂H₅ | |
| 110 | —CH₂—CO—OCH₂—C₂H₅ | |
| 111 | —CH₂—CO—OCH(CH₃)₂ | |
| 112 | —CH₂—CO—OCH₂—CH₂—C₂H₅ | |
| 113 | —CH₂—CO—OCH₂—CH(CH₃)₂ | |
| 114 | —CH₂—CO—OCH(CH₃)—C₂H₅ | |
| 115 | —CH₂—CO—OC(CH₃)₃ | |
| 116 | —CH₂—CO—OCH₂—CH₂—CH₂—C₂H₅ | |
| 117 | —CH(CH₃)—CO—OH | |
| 118 | —CH(CH₃)—CO—OCH₃ | oil |
| 119 | —CH(CH₃)—CO—OC₂H₅ | |
| 120 | —CH(CH₃)—CO—OCH₂—C₂H₅ | |
| 121 | —CH(CH₃)—CO—OCH(CH₃)₂ | |
| 122 | —CH(CH₃)—CO—OCH₂—CH₂—C₂H₅ | |
| 123 | —CH(CH₃)—CO—OCH₂—CH(CH₃)₂ | |
| 124 | —CH(CH₃)—CO—OCH(CH₃)—C₂H₅ | |
| 125 | —CH(CH₃)—CO—OC(CH₃)₃ | |
| 126 | —CH(CH₃)—CO—OCH₂—CH₂—CH₂—C₂H₅ | |
| 127 | —CH₂—CO—OCH₂—CH=CH₂ | |
| 128 | —CH₂—CO—OCH(CH₃)—CH=CH₂ | |
| 129 | —CH₂—CO—OCH₂—C(CH₃)=CH₂ | |

TABLE 1-continued

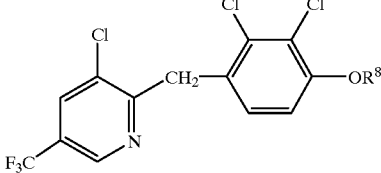

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 130 | —CH$_2$—CO—OCH$_2$—CH=CH—CH$_3$ | |
| 131 | —CH$_2$—CO—OCH$_2$—CH=C(CH$_3$)$_2$ | |
| 132 | —CH$_2$—CO—OCH$_2$—CH$_2$—CH=C(CH$_3$)$_2$ | |
| 133 | —CH(CH$_3$)—CO—OCH$_2$—CH=CH$_2$ | |
| 134 | —CH(CH$_3$)—CO—OCH(CH$_3$)—CH=CH$_2$ | |
| 135 | —CH(CH$_3$)—CO—OCH$_2$—C(CH$_3$)=CH$_2$ | |
| 136 | —CH(CH$_3$)—CO—OCH$_2$—CH=CH—CH$_3$ | |
| 137 | —CH(CH$_3$)—CO—OCH$_2$—CH=C(CH$_3$)$_2$ | |
| 138 | —CH(CH$_3$)—CO—OCH$_2$—CH$_2$—CH=C(CH$_3$)$_2$ | |
| 139 | —CH$_2$—CO—OCH$_2$—C≡CH | |
| 140 | —CH$_2$—CO—OCH(CH$_3$)—C≡CH | |
| 141 | —CH$_2$—CO—OCH$_2$—C≡C—CH$_3$ | |
| 142 | —CH(CH$_3$)—CO—OCH$_2$—C≡CH | |
| 143 | —CH(CH$_3$)—CO—OCH(CH$_3$)—C≡CH | |
| 144 | —CH(CH$_3$)—CO—OCH$_2$—C≡C—CH$_3$ | |
| 145 | —CH$_2$—CO—OCH$_2$—CH$_2$—OCH$_3$ | |
| 146 | —CH$_2$—CO—OCH$_2$—CH$_2$—OC$_2$H$_5$ | |
| 147 | —CH$_2$—CO—OCH$_2$—CH$_2$—OCH$_2$—C$_2$H$_5$ | |
| 148 | —CH$_2$—CO—OCH$_2$—CH$_2$—OCH(CH$_3$)$_2$ | |
| 149 | —CH(CH$_3$)—CO—OCH$_2$—CH$_2$—OCH$_3$ | |
| 150 | —CH(CH$_3$)—CO—OCH$_2$—CH$_2$—OC$_2$H$_5$ | |
| 151 | —CH(CH$_3$)—CO—OCH$_2$—CH$_2$—OCH$_2$—C$_2$H$_5$ | |
| 152 | —CH(CH$_3$)—CO—OCH$_2$—CH$_2$—OCH(CH$_3$)$_2$ | |
| 153 | —CH$_2$—CO—OCH$_2$—CF$_3$ | |
| 154 | —CH(CH$_3$)—CO—OCH$_2$—CF$_3$ | |
| 155 | —CH$_2$—CO—O-cyclopropyl | |
| 156 | —CH$_2$—CO—O-cyclobutyl | |
| 157 | —CH$_2$—CO—O-cyclopentyl | |
| 158 | —CH$_2$—CO—O-cyclohexyl | |
| 159 | —CH(CH$_3$)—CO—O-cyclopropyl | |
| 160 | —CH(CH$_3$)—CO—O-cyclobutyl | |
| 161 | —CH(CH$_3$)—CO—O-cyclopentyl | |
| 162 | —CH(CH$_3$)—CO—O-cyclohexyl | |
| 163 | —CH$_2$—CO—OCH$_2$—CO—OCH$_3$ | |
| 164 | —CH$_2$—CO—OCH$_2$—CO—OC$_2$H$_5$ | |
| 165 | —CH$_2$—CO—OCH(CH$_3$)—CO—OCH$_3$ | |
| 166 | —CH$_2$—CO—OCH(CH$_3$)—CO—OC$_2$H$_5$ | |
| 167 | —CH(CH$_3$)—CO—OCH$_2$—CO—OCH$_3$ | |
| 168 | —CH(CH$_3$)—CO—OCH$_2$—CO—OC$_2$H$_5$ | |
| 169 | —CH(CH$_3$)—CO—OCH(CH$_3$)—CO—OCH$_3$ | |
| 170 | —CH(CH$_3$)—CO—OCH(CH$_3$)—CO—OC$_2$H$_5$ | |
| 171 | —CH$_2$—CO—OCH$_2$—CO—OCH$_2$—CH=CH$_2$ | |
| 172 | —CH$_2$—CO—OCH(CH$_3$)—CO—OCH$_2$—CH=CH$_2$ | |
| 173 | —CH(CH$_3$)—CO—OCH$_2$—CO—OCH$_2$—CH=CH$_2$ | |
| 174 | —CH(CH$_3$)—CO—OCH(CH$_3$)—CO—OCH$_2$—CH=CH$_2$ | |
| 175 | —CH$_2$—CO—OCH$_2$—CO—OCH$_2$—C≡CH | |
| 176 | —CH$_2$—CO—OCH$_2$—CO—OCH(CH$_3$)—C≡CH | |
| 177 | —CH$_2$—CO—OCH(CH$_3$)—CO—OCH$_2$—C≡CH | |
| 178 | —CH$_2$—CO—OCH(CH$_3$)—CO—OCH(CH$_3$)—C≡CH | |
| 179 | —CH(CH$_3$)—CO—OCH$_2$—CO—OCH$_2$—C≡CH | |
| 180 | —CH(CH$_3$)—CO—OCH$_2$—CO—OCH(CH$_3$)—C≡CH | |
| 181 | —CH(CH$_3$)—CO—OCH(CH$_3$)—CO—OCH$_2$—C≡CH | |
| 182 | —CH(CH$_3$)—CO—OCH(CH$_3$)—CO—OCH(CH$_3$)—C≡CH | |
| 183 | —CH$_2$—CO—OCH$_2$—COOH | |
| 184 | —CH(CH$_3$)—CO—OCH$_2$—COOH | |
| 185 | —CH$_2$—CO—OCH(CH$_3$)—COOH | |
| 186 | —CH(CH$_3$)—CO—OCH(CH$_3$)—COOH | |
| 187 | —CH$_2$—CO—O-(oxetan-3-yl) | |
| 188 | —CH(CH$_3$)—CO—O-(oxetan-3-yl) | |
| 189 | —CH$_2$—CO—O-phenyl | |
| 190 | —CH(CH$_3$)—CO—O-phenyl | |
| 191 | —CH$_2$—CO—O-(o-chlorophenyl) | |
| 192 | —CH$_2$—CO—O-(m-chlorophenyl) | |

TABLE 1-continued

I {n = O; X = CH₂; R¹ = CF₃; R², R³, R⁴ = Cl; R⁵ = OR⁸; R⁶, R⁷ = H}

| No. | —R⁸ | Mp./¹H NMR (in CDCl₃) [ppm] |
|---|---|---|
| 193 | —CH₂—CO—O-(p-chlorophenyl) | |
| 194 | —CH(CH₃)—CO—O-(o-chlorophenyl) | |
| 195 | —CH(CH₃)—CO—O-(m-chlorophenyl) | |
| 196 | —CH(CH₃)—CO—O-(p-chlorophenyl) | |
| 197 | —CH₂—CO—O-(o-methylphenyl) | |
| 198 | —CH₂—CO—O-(m-methylphenyl) | |
| 199 | —CH₂—CO—O-(p-methylphenyl) | |
| 200 | —CH(CH₃)—CO—O-(o-methylphenyl) | |
| 201 | —CH(CH₃)—CO—O-(m-methylphenyl) | |
| 202 | —CH(CH₃)—CO—O-(p-methylphenyl) | |
| 203 | —CH₂—CO—O—(o-OCF₃-phenyl) | |
| 204 | —CH₂—CO—O—(m-OCF₃-phenyl) | |
| 205 | —CH₂—CO—O—(p-OCF₃-phenyl) | |
| 206 | —CH(CH₃)—CO—O—(o-OCF₃-phenyl) | |
| 207 | —CH(CH₃)—CO—O—(m-OCF₃-phenyl) | |
| 208 | —CH(CH₃)—CO—O—(p-OCF₃-phenyl) | |
| 209 | —CH₂—CO—O—(o-(OCH₂—CO—OCH₃)-phenyl) | |

TABLE 1-continued

[Structure: 3-chloro-5-(trifluoromethyl)pyridin-2-yl-CH₂-linked to 2,3-dichloro-4-(OR⁸)-phenyl]

I {n = O; X = CH₂; R¹ = CF₃; R², R³, R⁴ = Cl; R⁵ = OR⁸; R⁶, R⁷ = H}

| No. | —R⁸ | Mp./¹H NMR (in CDCl₃) [ppm] |
|---|---|---|
| 210 | —CH₂—CO—O—(3-OCH₂—CO—OCH₃-phenyl) | |
| 211 | —CH₂—CO—O—(4-OCH₂—CO—OCH₃-phenyl) | |
| 212 | —CH(CH₃)—CO—O—(2-OCH₂—CO—OCH₃-phenyl) | |
| 213 | —CH(CH₃)—CO—O—(3-OCH₂—CO—OCH₃-phenyl) | |
| 214 | —CH(CH₃)—CO—O—(4-OCH₂—CO—OCH₃-phenyl) | |
| 215 | —CH₂—CO—O—(2-OCH(CH₃)—CO—OCH₃-phenyl) | |
| 216 | —CH₂—CO—O—(3-OCH(CH₃)—CO—OCH₃-phenyl) | |
| 217 | —CH₂—CO—O—(4-OCH(CH₃)—CO—OCH₃-phenyl) | |
| 218 | —CH(CH₃)—CO—O—(2-OCH(CH₃)—CO—OCH₃-phenyl) | |

TABLE 1-continued

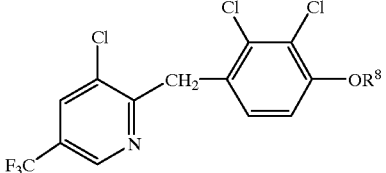

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 219 | 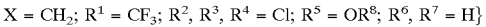 | |
| 220 | 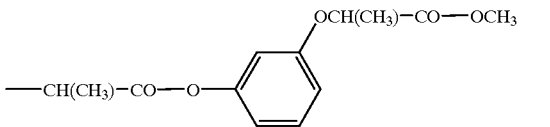 | |
| 221 | —CH$_2$—CO—O-(o-nitrophenyl) | |
| 222 | —CH$_2$—CO—O-(m-nitrophenyl) | |
| 223 | —CH$_2$—CO—O-(p-nitrophenyl) | |
| 224 | —CH(CH$_3$)—CO—O-(o-nitrophenyl) | |
| 225 | —CH(CH$_3$)—CO—O-(m-nitrophenyl) | |
| 226 | —CH(CH$_3$)—CO—O-(p-nitrophenyl) | |
| 227 | —CH$_2$—CO—O-(o-cyanophenyl) | |
| 228 | —CH$_2$—CO—O-(m-cyanophenyl) | |
| 229 | —CH$_2$—CO—O-(p-cyanophenyl) | |
| 230 | —CH(CH$_3$)—CO—O-(o-cyanophenyl) | |
| 231 | —CH(CH$_3$)—CO—O-(m-cyanophenyl) | |
| 232 | —CH(CH$_3$)—CO—O-(p-cyanophenyl) | |
| 233 | 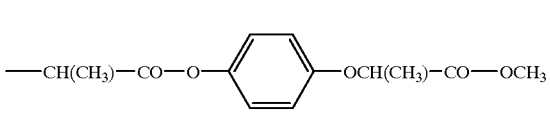 | |
| 234 | 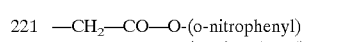 | |
| 235 | 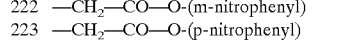 | |
| 236 | 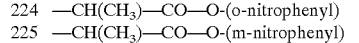 | |
| 237 | 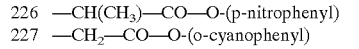 | |

TABLE 1-continued

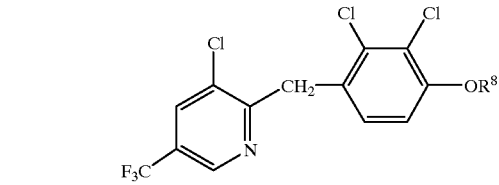

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 238 | —CH(CH$_3$)—CO—O—⟨C$_6$H$_4$⟩—CO—OCH$_3$ | |
| 239 | —CH$_2$—CO—OCH$_2$-phenyl | |
| 240 | —CH(CH$_3$)—CO—OCH$_2$-phenyl | |
| 241 | —CH$_2$—CO—OCH$_2$-(o-chlorophenyl) | |
| 242 | —CH$_2$—CO—OCH$_2$-(m-chlorophenyl) | |
| 243 | —CH$_2$—CO—OCH$_2$-(p-chlorophenyl) | |
| 244 | —CH(CH$_3$)—CO—OCH$_2$-(o-chlorophenyl) | |
| 245 | —CH(CH$_3$)—CO—OCH$_2$-(m-chlorophenyl) | |
| 246 | —CH(CH$_3$)—CO—OCH$_2$-(p-chlorophenyl) | |
| 247 | —CH$_2$—CO—OCH$_2$-(o-methylphenyl) | |
| 248 | —CH$_2$—CO—OCH$_2$-(m-methylphenyl) | |
| 249 | —CH$_2$—CO—OCH$_2$-(p-methylphenyl) | |
| 250 | —CH(CH$_3$)—CO—OCH$_2$-(o-methylphenyl) | |
| 251 | —CH(CH$_3$)—CO—OCH$_2$-(m-methylphenyl) | |
| 252 | —CH(CH$_3$)—CO—OCH$_2$-(p-methylphenyl) | |
| 253 | —CH$_2$—CO—OCH$_2$-(o-OCF$_3$-phenyl) | |
| 254 | —CH$_2$—CO—OCH$_2$-(m-OCF$_3$-phenyl) | |
| 255 | —CH$_2$—CO—OCH$_2$-(p-OCF$_3$-phenyl) | |
| 256 | —CH(CH$_3$)—CO—OCH$_2$-(o-OCF$_3$-phenyl) | |
| 257 | —CH(CH$_3$)—CO—OCH$_2$-(m-OCF$_3$-phenyl) | |
| 258 | —CH(CH$_3$)—CO—OCH$_2$-(p-OCF$_3$-phenyl) | |

TABLE 1-continued

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 259 | —CH$_2$—CO—OCH$_2$—(2-(OCH$_2$—CO—OCH$_3$)C$_6$H$_4$) | |
| 260 | —CH$_2$—CO—OCH$_2$—(3-(OCH$_2$—CO—OCH$_3$)C$_6$H$_4$) | |
| 261 | —CH$_2$—CO—OCH$_2$—(4-(OCH$_2$—CO—OCH$_3$)C$_6$H$_4$) | |
| 262 | —CH(CH$_3$)—CO—OCH$_2$—(2-(OCH$_2$—CO—OCH$_3$)C$_6$H$_4$) | |
| 263 | —CH(CH$_3$)—CO—OCH$_2$—(3-(OCH$_2$—CO—OCH$_3$)C$_6$H$_4$) | |
| 264 | —CH(CH$_3$)—CO—OCH$_2$—(4-(OCH$_2$—CO—OCH$_3$)C$_6$H$_4$) | |
| 265 | —CH$_2$—CO—OCH$_2$—(2-(OCH(CH$_3$)—CO—OCH$_3$)C$_6$H$_4$) | |
| 266 | —CH$_2$—CO—OCH$_2$—(3-(OCH(CH$_3$)—CO—OCH$_3$)C$_6$H$_4$) | |
| 267 | —CH$_2$—CO—OCH$_2$—(4-(OCH(CH$_3$)—CO—OCH$_3$)C$_6$H$_4$) | |

TABLE 1-continued

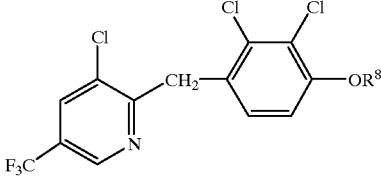

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 268 | 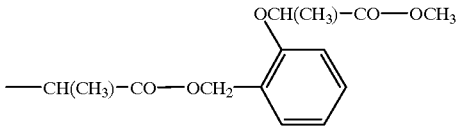 | |
| 269 | 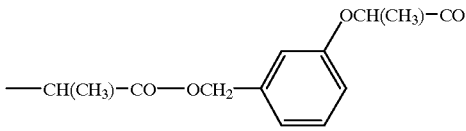 | |
| 270 | 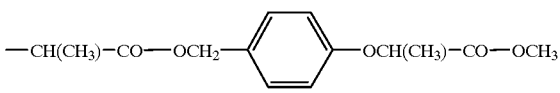 | |
| 271 | —CH$_2$—CO—OCH$_2$-(o-nitrophenyl) | |
| 272 | —CH$_2$—CO—OCH$_2$-(m-nitrophenyl) | |
| 273 | —CH$_2$—CO—OCH$_2$-(p-nitrophenyl) | |
| 274 | —CH(CH$_3$)—CO—OCH$_2$-(o-nitrophenyl) | |
| 275 | —CH(CH$_3$)—CO—OCH$_2$-(m-nitrophenyl) | |
| 276 | —CH(CH$_3$)—CO—OCH$_2$-(p-nitrophenyl) | |
| 277 | —CH$_2$—CO—OCH$_2$-(o-cyanophenyl) | |
| 278 | —CH$_2$—CO—OCH$_2$-(m-cyanophenyl) | |
| 279 | —CH$_2$—CO—OCH$_2$-(p-cyanophenyl) | |
| 280 | —CH(CH$_3$)—CO—OCH$_2$-(o-cyanophenyl) | |
| 281 | —CH(CH$_3$)—CO—OCH$_2$-(m-cyanophenyl) | |
| 282 | —CH(CH$_3$)—CO—OCH$_2$-(p-cyanophenyl) | |
| 283 | 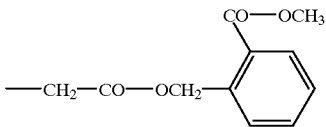 | |
| 284 | 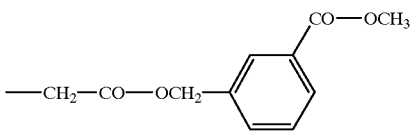 | |
| 285 | 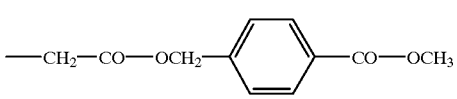 | |
| 286 | 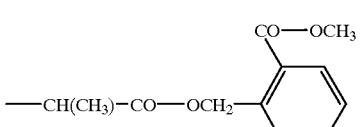 | |

TABLE 1-continued
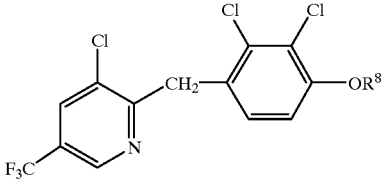
I {n = O; X = CH₂; R¹ = CF₃; R², R³, R⁴ = Cl; R⁵ = OR⁸; R⁶, R⁷ = H}
| No. | —R⁸ | Mp./¹H NMR (in CDCl₃) [ppm] |
|---|---|---|
| 287 | 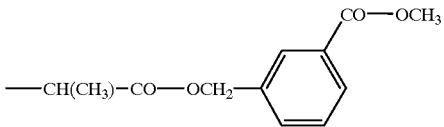 | |
| 288 | 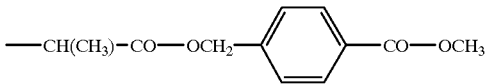 | |
| 289 | 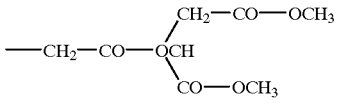 | |
| 290 | 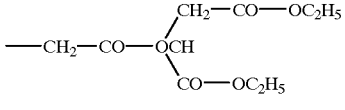 | |
| 291 | 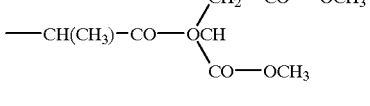 | |
| 292 | 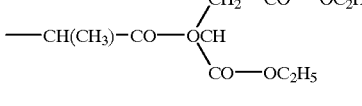 | |
| 293 | 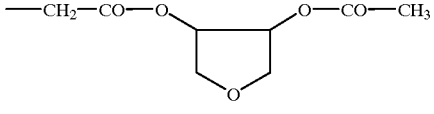 | |
| 294 | 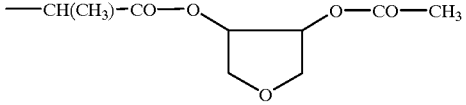 | |
| 295 | —CH₂—CO—NH₂ | |
| 296 | —CH(CH₃)—CO—NH₂ | |
| 297 | —CH₂—CO—NH(CH₃) | |
| 298 | —CH(CH₃)—CO—NH(CH₃) | |
| 299 | —CH₂—CO—N(CH₃)₂ | |
| 300 | —CH(CH₃)—CO—N(CH₃)₂ | |
| 301 | —CH₂—CO—N(CH₃)—CH₂—CO—OCH₃ | |
| 302 | —CH₂—CO—N(CH₃)—CH₂—CO—OC₂H₅ | |
| 303 | —CH₂—CO—N(CH₃)—CH(CH₃)—CO—OCH₃ | |
| 304 | —CH₂—CO—N(CH₃)—CH(CH₃)—CO—OC₂H₅ | |
| 305 | —CH(CH₃)—CO—N(CH₃)—CH₂—CO—OCH₃ | |
| 306 | —CH(CH₃)—CO—N(CH₃)—CH₂—CO—OC₂H₅ | |
| 307 | —CH(CH₃)—CO—N(CH₃)—CH(CH₃)—CO—OCH₃ | |
| 308 | —CH(CH₃)—CO—N(CH₃)—CH(CH₃)—CO—OC₂H₅ | |

TABLE 1-continued

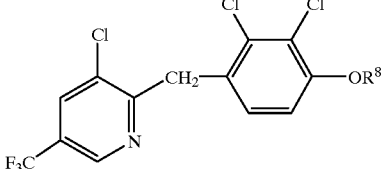

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 309 | —CH$_2$—CO—N(CH$_3$)-phenyl | |
| 310 | —CH(CH$_3$)—CO—N(CH$_3$)-phenyl | |
| 311 | —CH$_2$—CO—NH-phenyl | |
| 312 | —CH(CH$_3$)—CO—NH-phenyl | |
| 313 | —CH$_2$—CO—N(CH$_3$)—CH$_2$-phenyl | |
| 314 | —CH(CH$_3$)—CO—N(CH$_3$)—CH$_2$-phenyl | |
| 315 | —CH$_2$—CO—NH—CH$_2$-phenyl | |
| 316 | —CH(CH$_3$)—CO—NH—CH$_2$-phenyl | |
| 317 | —CH$_2$—CO-(pyrrolidin-1-yl) | |
| 318 | —CH(CH$_3$)—CO-(pyrrolidin-1-yl) | |
| 319 | —CH$_2$—CO-(piperidin-1-yl) | |
| 320 | —CH(CH$_3$)—CO-(piperidin-1-yl) | |
| 321 | —CH$_2$—CO-(morpholin-4-yl) | |
| 322 | —CH(CH$_3$)—CO-(morpholin-4-yl) | |
| 323 | 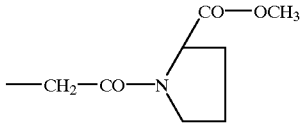 | |
| 324 | 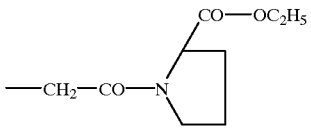 | |
| 325 | 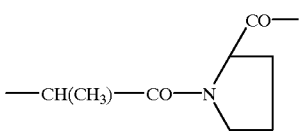 | |
| 326 | 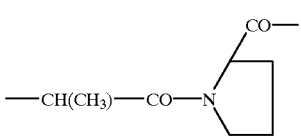 | |
| 327 | —CH$_2$—CO—H | |
| 328 | —CH$_2$—CO—CH$_3$ | |
| 329 | —CH(CH$_3$)—CO—H | |
| 330 | —CH(CH$_3$)—CO—CH$_3$ | |
| 331 | —CH$_2$—CH=N—OH | |
| 332 | —CH(CH$_3$)—CH=N—OH | |
| 333 | —CH$_2$—C(CH$_3$)=N—OH | |
| 334 | —CH(CH$_3$)—C(CH$_3$)=N—OH | |
| 335 | —CH$_2$—CH=N—OCH$_3$ | |
| 336 | —CH(CH$_3$)—CH=N—OCH$_3$ | |
| 337 | —CH$_2$—C(CH$_3$)=N—OCH$_3$ | |
| 338 | —CH(CH$_3$)—C(CH$_3$)=N—OCH$_3$ | |
| 339 | —CH$_2$—CH=N—OCH$_2$—CH=CH$_2$ | |
| 340 | —CH(CH$_3$)—CH=N—OCH$_2$—CH=CH$_2$ | |
| 341 | —CH$_2$—C(CH$_3$)=N—OCH$_2$—CH=CH$_2$ | |
| 342 | —CH(CH$_3$)—C(CH$_3$)=N—OCH$_2$—CH=CH$_2$ | |
| 343 | —CH$_2$—CH=N—OCH$_2$—CO—OCH$_3$ | |
| 344 | —CH$_2$—CH=N—OCH$_2$—CO—OC$_2$H$_5$ | |
| 345 | —CH(CH$_3$)—CH=N—OCH$_2$—CO—OCH$_3$ | |

TABLE 1-continued

[Structure: 3-chloro-5-(trifluoromethyl)pyridin-2-yl-CH₂ linked to 2,3-dichloro-4-(OR⁸)phenyl]

I {n = 0; X = CH$_2$; R$^1$ = CF$_3$; R$^2$, R$^3$, R$^4$ = Cl; R$^5$ = OR$^8$; R$^6$, R$^7$ = H}

| No. | —R⁸ | Mp./¹H NMR (in CDCl₃) [ppm] |
|---|---|---|
| 346 | —CH(CH₃)—CH=N—OCH₂—CO—OC₂H₅ | |
| 347 | —CH₂—C(CH₃)=N—OCH₂—CO—OCH₃ | |
| 348 | —CH₂—C(CH₃)=N—OCH₂—CO—OC₂H₅ | |
| 349 | —CH(CH₃)—C(CH₃)=N—OCH₂—CO—OCH₃ | |
| 350 | —CH(CH₃)—C(CH₃)=N—OCH₂—CO—OC₂H₅ | |
| 351 | —CH₂—CH=N—OCH(CH₃)—CO—OCH₃ | |
| 352 | —CH₂—CH=N—OCH(CH₃)—CO—OC₂H₅ | |
| 353 | —CH(CH₃)—CH=N—OCH(CH₃)—CO—OCH₃ | |
| 354 | —CH(CH₃)—CH=N—OCH(CH₃)—CO—OC₂H₅ | |
| 355 | —CH₂—C(CH₃)=N—OCH(CH₃)—CO—OCH₃ | |
| 356 | —CH₂—C(CH₃)=N—OCH(CH₃)—CO—OC₂H₅ | |
| 357 | —CH(CH₃)—C(CH₃)=N—OCH(CH₃)—CO—OCH₃ | |
| 358 | —CH(CH₃)—C(CH₃)=N—OCH(CH₃)—CO—OC₂H₅ | |
| 359 | —CH₂—CO—CO—OCH₃ | |
| 360 | —CH₂—CO—CO—OC₂H₅ | |
| 361 | —CH₂—CO—CO—OCH₂—C₂H₅ | |
| 362 | —CH₂—CO—CO—OCH(CH₃)₂ | |
| 363 | —CH₂—CO—CO—OCH₂—CH₂—C₂H₅ | |
| 364 | —CH₂—CO—CO—OCH₂—CH(CH₃)₂ | |
| 365 | —CH₂—CO—CO—OCH(CH₃)—C₂H₅ | |
| 366 | —CH₂—CO—CO—OC(CH₃)₃ | |
| 367 | —CH(CH₃)—CO—CO—OCH₃ | |
| 368 | —CH(CH₃)—CO—CO—OC₂H₅ | |
| 369 | —CH₂—C(=N—OCH₃)—CO—OCH₃ | 113° C. |
| 370 | —CH₂—C(=N—OCH₃)—CO—OC₂H₅ | |
| 371 | —CH₂—C(=N—OC₂H₅)—CO—OCH₃ | |
| 372 | —CH₂—C(=N—OC₂H₅)—CO—OC₂H₅ | |
| 373 | —CH₂—C(=N—OCH₂—CH=CH₂)—CO—OCH₃ | |
| 374 | —CH₂—C(=N—OCH₂—CH=CH₂)—CO—OC₂H₅ | |
| 375 | —CH₂—C(=N—OCH₂-phenyl)—CO—OCH₃ | |
| 376 | —CH₂—C(=N—OCH₂-phenyl)—CO—OC₂H₅ | |

TABLE 1-continued

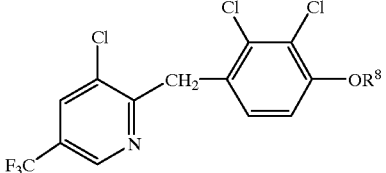

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 377 | —CH(CH$_3$)—C(=N—OCH$_3$)—CO—OCH$_3$ | |
| 378 | —CH(CH$_3$)—C(=N—OC$_2$H$_5$)—CO—OCH$_3$ | |
| 379 | —CH(CH$_3$)—C(=N—OCH$_3$)—CO—OC$_2$H$_5$ | |
| 380 | —CH(CH$_3$)—C(=N—OC$_2$H$_5$)—CO—OC$_2$H$_5$ | |
| 381 | —CH(CH$_3$)—C(=N—OCH$_2$—CH=CH$_2$)—CO—OCH$_3$ | |
| 382 | —CH(CH$_3$)—C(=N—OCH$_2$—CH=CH$_2$)—CO—OC$_2$H$_5$ | |
| 383 | —CH(CH$_3$)—C(=N—OCH$_2$-phenyl)—CO—OCH$_3$ | |
| 384 | —CH(CH$_3$)—C(=N—OCH$_2$-phenyl)—CO—OC$_2$H$_5$ | |
| 385 | —CH$_2$—CO—N(OCH$_3$)(CH$_2$—CO—OCH$_3$) | |
| 386 | —CH$_2$—CO—N(OCH$_3$)(CH$_2$—CO—OC$_2$H$_5$) | |
| 387 | —CH$_2$—CO—N(OCH$_3$)(CH(CH$_3$)—CO—OCH$_3$) | |
| 388 | —CH$_2$—CO—N(OCH$_3$)(CH(CH$_3$)—CO—OC$_2$H$_5$) | |

TABLE 1-continued

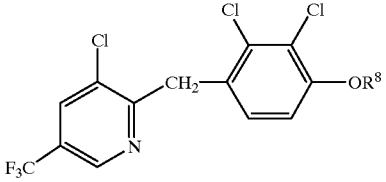

I {n = O; X = CH$_2$; R$^1$ = CF$_3$; R$^2$, R$^3$, R$^4$ = Cl; R$^5$ = OR$^8$; R$^6$, R$^7$ = H}

| No. | —R$^8$ | Mp./$^1$H NMR (in CDCl$_3$) [ppm] |
|---|---|---|
| 389 | —CH(CH$_3$)—CO—N(OCH$_3$)(CH$_2$—CO—OCH$_3$) | |
| 390 | —CH(CH$_3$)—CO—N(OCH$_3$)(CH$_2$—CO—OC$_2$H$_5$) | |
| 391 | —CH(CH$_3$)—CO—N(OCH$_3$)(CH(CH$_3$)—CO—OCH$_3$) | |
| 392 | —CH(CH$_3$)—CO—N(OCH$_3$)(CH(CH$_3$)—CO—OC$_2$H$_5$) | |
| 393 | —CH$_2$—C(=N—OCH$_3$)(OCH$_2$—CO—OCH$_3$) | |
| 394 | —CH$_2$—C(=N—OCH$_3$)(OCH$_2$—CO—OC$_2$H$_5$) | |
| 395 | —CH$_2$—C(=N—OCH$_3$)(OCH(CH$_3$)—CO—OCH$_3$) | |
| 396 | —CH$_2$—C(=N—OCH$_3$)(OCH(CH$_3$)—CO—OC$_2$H$_5$) | |
| 397 | —CH(CH$_3$)—C(=N—OCH$_3$)(OCH$_2$—CO—OCH$_3$) | |
| 398 | —CH(CH$_3$)—C(=N—OCH$_3$)(OCH$_2$—CO—OC$_2$H$_5$) | |

TABLE 1-continued
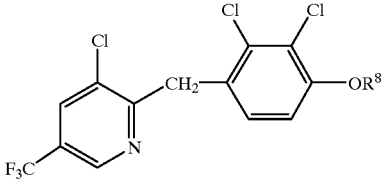
I {n = O; X = CH$_2$; R$^1$ = CF$_3$; R$^2$, R$^3$, R$^4$ = Cl; R$^5$ = OR$^8$; R$^6$, R$^7$ = H}
| No. | —R$^8$ | Mp./$^1$H NMR (in CDCl$_3$) [ppm] |
|---|---|---|
| 399 | —CH(CH$_3$)—C(=N—OCH$_3$)—OCH(CH$_3$)—CO—OCH$_3$ | |
| 400 | —CH(CH$_3$)—C(=N—OCH$_3$)—OCH(CH$_3$)—CO—OC$_2$H$_5$ | |
| 401 | 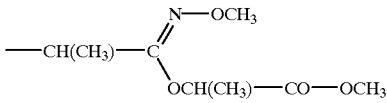 | |
| 402 | 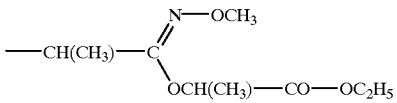 | |
| 403 | 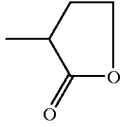 | |
| 404 | 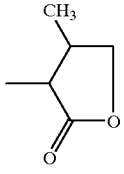 | |
| 405 | 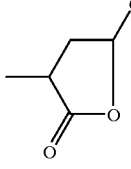 | |
| 406 | 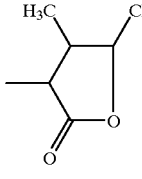 | |

TABLE 1-continued
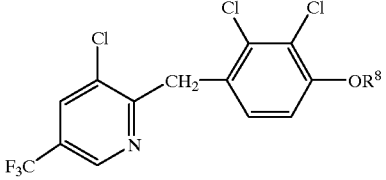
I {n = O; X = CH$_2$; R$^1$ = CF$_3$; R$^2$, R$^3$, R$^4$ = Cl; R$^5$ = OR$^8$; R$^6$, R$^7$ = H}
| No. | —R$^8$ | Mp./$^1$H NMR (in CDCl$_3$) [ppm] |
|---|---|---|
| 407 | 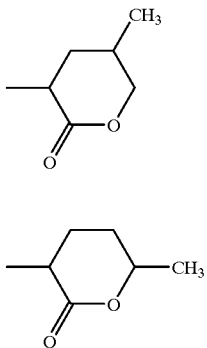 | |
| 408 | 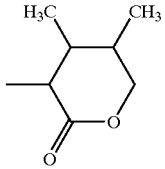 | |
| 419 | 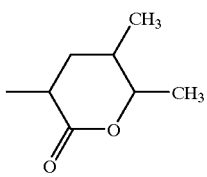 | |
| 410 | 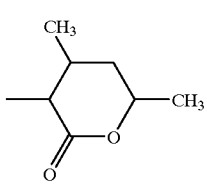 | |
| 411 | 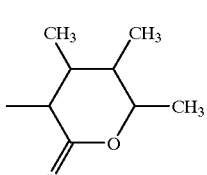 | |
| 412 | | |

TABLE 2

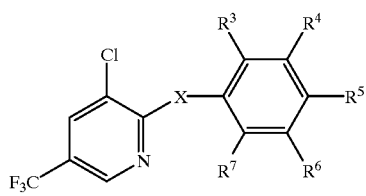

I {n = O; R$^1$ = CF$_3$; R$^2$ = Cl}

| No. | X | R$^3$ | R$^4$ | R$^5$ | R$^6$ | R$^7$ | Mp. [° C.] |
|---|---|---|---|---|---|---|---|
| 451 | CH$_2$ | H | H | Cl | H | H | 56 |
| 452 | C=O | H | H | Cl | H | H | oil |
| 453 | CH—OH | H | H | Cl | H | H | oil |
| 454 | CH—OCH$_3$ | H | H | Cl | H | H | oil |
| 455 | CH—CN | H | H | Cl | H | H | oil |
| 456 | CH—CO—NH$_2$ | H | H | Cl | H | H | 136 |
| 457 | CH—CO—OCH$_3$ | H | H | Cl | H | H | 104 |
| 458 | CH$_2$ | Cl | Cl | H | H | H | oil |
| 459 | CH—CN | Cl | Cl | H | H | H | oil |
| 460 | C=O | H | Br | OCH$_3$ | H | H | 72 |
| 461 | C=O | H | H | OCH$_2$—C≡CH | H | H | 70 |
| 462 | C=O | H | H | OCH(CH$_3$)—CO—OCH$_3$ | H | H | 89 |
| 463 | CH$_2$ | H | CF$_3$ | H | H | H | oil |
| 464 | CH$_2$ | H | Cl | Cl | H | H | oil |
| 465 | CH$_2$ | Cl | H | Cl | H | H | oil |
| 466 | CH$_2$ | Cl | H | H | H | H | oil |
| 467 | CH$_2$ | H | Cl | H | H | H | oil |
| 468 | CH$_2$ | F | H | H | H | Cl | oil |
| 469 | CH$_2$ | H | H | H | H | H | oil |
| 470 | CH$_2$ | H | H | NO$_2$ | H | H | 74 |
| 471 | CH$_2$ | H | H | NH$_2$ | H | H | 73 |
| 472 | CH—CN | H | Cl | OCH$_3$ | H | H | 100 |
| 473 | C=O | H | Cl | OCH$_3$ | H | H | 83 |
| 474 | CH—OH | H | Cl | OCH(CH$_3$)$_2$ | H | H | 65 |
| 475 | C=O | H | Cl | OCH(CH$_3$)—C≡CH | H | H | 95 |
| 476 | CH—CN | H | H | CN | H | H | oil |
| 477 | CH—CN | F | H | H | H | Cl | 106 |
| 478 | C=O | H | Cl | H | H | H | oil |
| 479 | CH—CN | H | Cl | H | H | H | 74 |
| 480 | CH—CN | Cl | H | H | H | H | 60 |
| 481 | CH—CN | O—CH$_3$ | H | H | H | H | 58 |
| 482 | CH—CN | H | H | CH$_3$ | H | H | 74 |
| 483 | CH—CN | Cl | H | Cl | H | H | 85 |
| 484 | CH—CN | H | Cl | Cl | H | H | oil |
| 485 | CH—CN | NO$_2$ | H | H | H | H | 94 |
| 486 | CH—CN | H | H | H | H | H | 72 |
| 487 | CH—CN | H | H | NO$_2$ | H | H | 112 |
| 488 | CH—CN | H | CF$_3$ | H | H | H | oil |
| 489 | CH—CN | Cl | Cl | OCH$_3$ | H | H | 176 |
| 490 | C=O | Cl | Cl | OCH(CH$_3$)—CO—OCH$_3$ | H | H | oil |
| 491 | CH$_2$ | H | H | CH$_3$ | H | H | 40 |
| 492 | CH$_2$ | H | OH | H | H | H | 83 |
| 493 | CH$_2$ | H | OCH$_3$ | H | H | H | oil |
| 494 | CH$_2$ | H | H | COOH | H | H | 176 |
| 495 | CH$_2$ | H | H | CO—OCH(CH$_3$)$_2$ | H | H | 74 |
| 496 | CH$_2$ | H | H | N(SO$_2$—CH$_3$)$_2$ | H | H | oil |
| 497 | CH—Cl | Cl | Cl | OCH$_3$ | H | H | 134 |
| 498 | CH—Br | Cl | Cl | OCH$_3$ | H | H | 105 |
| 499 | CH—CH$_3$ | Cl | Cl | OCH$_3$ | H | H | 107 |
| 500 | CH$_2$ | Cl | H | NH—CO—CH$_3$ | OH | H | 191 |
| 501 | CH$_2$ | H | H | H | COOH | H | 125 |
| 502 | CH$_2$ | H | H | H | CO—OC$_2$H$_5$ | H | 41 |
| 503 | CH$_2$ | H | H | NO$_2$ | COOH | H | 264 |
| 504 | CH$_2$ | H | H | NO$_2$ | CO—OC$_2$H$_5$ | H | oil |
| 505 | CH$_2$ | H | NO$_2$ | H | CO—OC$_2$H$_5$ | H | 89 |
| 506 | CH$_2$ | H | H | NO$_2$ | OH | H | 145 |
| 507 | CH$_2$ | NO$_2$ | H | H | OCH$_3$ | H | 73 |
| 508 | CH$_2$ | H | OCH$_3$ | NO$_2$ | H | H | oil |
| 509 | CH$_2$ | NO$_2$ | H | NO$_2$ | OCH$_3$ | H | 140 |
| 510 | CH$_2$ | H | H | H | OCH$_3$ | NO$_2$ | 101 |

USE EXAMPLES

Herbicidal Activity

The herbicidal activity of the substituted 2-benz(o)ylpyridines I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transluscent plastic hoods until the plants had rooted. This cover causes uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment. The rate of application for the post-emergence treatment was 0.125, 0.0625, 0.0078 or 0.0039 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| Glycine max | soybeans |
| Abutilon theophrasti | velvet leaf |
| Solanum nigrum | black nightshade |
| Polygonum persicaria | ladysthumb |
| Veronica spec. | speedwell |

The compounds No. 118 and 369, applied post-emergence, showed a very good herbicidal activity against Abutilon theophrasti, Solanum nigrum, Polygonum persicaria and Veronica spec. at rates of application of 7.8 and 3.9 g/ha a.s.

The compound No. 460, applied post-emergence, showed very good selective herbicidal activity against Abutilon theophrasti, Solanum nigrum and Veronica spec. in soya crops, which were damaged only to a small extent, at rates of application of 0.125 and 0.0625 kg/ha a.s.

USE EXAMPLES

Desiccant/Defoliant Activity

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to runoff point with aqueous preparations of the active compounds (with an addition of 0.15% by weight of the fatty alcohol alkoxide Plurafac® LF 700[1]), based on the spray mixture). The amount of water applied was 1000 l/ha (converted). After 13 days, the number of leaves shed and the degree of defoliation in % were determined.

No leaves were shed in the untreated control plants.

[1])a low-foam, nonionic surfactant from BASF AG

We claim:

1. Substituted 2-benz(o)ylpyridines of the formula I

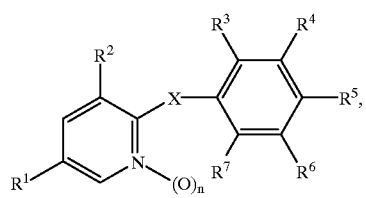

where:

n is 0 or 1;

X is methylene;

$R^1$ is $C_1-C_4$-haloalkyl;

$R^2$ is halogen;

$R^3$ is halogen;

$R^4$ is halogen;

$R^5$ is —$OR^8$, where $R^8$ is $C_3-C_8$-alkynyl, $(C_1-C_8$-alkoxy)carbonyl-$C_1-C_6$-alkyl or

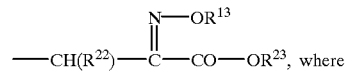

$R^{13}$ is hydrogen, $C_1-C_8$-alkyl, $C_3-C_8$-alkenyl, $C_3-C_8$-alkynyl or $(C_1-C_4$-alkoxy)carbonyl-$C_1-C_4$-alkyl, and $R^{22}$ and $R^{23}$ independently of one another are each hydrogen, $C_1-C_8$-alkyl, $C_3-C_8$-alkenyl or $C_3-C_8$-alkynyl;

$R^6$ is hydrogen or halogen, and $R^7$ is hydrogen or halogen;

and the agriculturally useful salts of the compounds I.

2. A herbicidal composition comprising a herbicidally effective amount of at least one 2-benz(o)ylpyridine of formula I or an agriculturally useful salt of I, defined in claim 1, and at least one inert liquid or solid carrier and, if desired, at least one surfactant.

3. A composition for the dessiccation and/or defoliation of plants, comprising such an amount of at least one 2-benz(o)ylpyridine of formula I or an agriculturally useful salt of I, defined in claim 1, that it acts as a dessicant and/or defoliant, and at least one inert liquid or solid carrier and, if desired, at least one surfactant.

4. A method for controlling undesirable vegetation, which comprises allowing a herbicidally effective amount of at least one 2-benz(o)ylpyridine of formula I or an agriculturally useful salt of I, defined in claim 1, to act on plants, their habitat or on seeds.

5. A method for the dessication or defoliation of plants, which comprises allowing such an amount of at least one substituted 2-benz(o)ylpyridine of formula I or an agriculturally useful salt of I, defined in claim 1, to act on plants that it has a dessicant and/or defoliant action.

6. A method as claimed in claim 5, wherein cotton is treated.

7. A process for preparing the 2-benz(o)ylpyridine of formula I defined in claim 1, which comprises reacting a pyridine of formula II

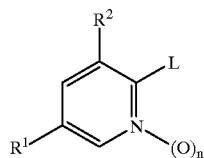

II in the presence of a base with a benzylnitrile of formula III

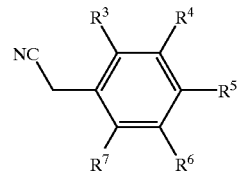

III and hydrolyzing and decarboxylating the product where X=CH—CN by means of an aqueous acid.

* * * * *

UNITED STATES PATENT AND TRADEMARK OFFICE
CERTIFICATE OF CORRECTION

PATENT NO. : 6,337,305
DATED : January 8, 2002
INVENTOR(S) : Schaefer et al.

It is certified that error appears in the above-identified patent and that said Letters Patent is hereby corrected as shown below:

<u>Title page,</u>
Item [75], Inventors, "Weimheim" should read -- Weinheim --.

<u>Column 70,</u>
Line 55, "2-benz" should read -- 2-benz- --.

Signed and Sealed this

Seventh Day of May, 2002

Attest:

Attesting Officer

JAMES E. ROGAN
*Director of the United States Patent and Trademark Office*